US009204063B2

United States Patent
Itani et al.

(10) Patent No.: US 9,204,063 B2
(45) Date of Patent: Dec. 1, 2015

(54) ELECTROMAGNETIC WAVE IMAGING APPARATUS

(75) Inventors: Norihiko Itani, Kawasaki (JP); Kazunori Maruyama, Kawasaki (JP); Shinya Hasegawa, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 1036 days.

(21) Appl. No.: 13/251,670

(22) Filed: Oct. 3, 2011

(65) Prior Publication Data

US 2012/0120231 A1  May 17, 2012

(30) Foreign Application Priority Data

Nov. 15, 2010 (JP) ................................ 2010-254401
Feb. 14, 2011 (JP) ................................ 2011-028349

(51) Int. Cl.

| | |
|---|---|
| *H04N 7/18* | (2006.01) |
| *H04N 5/335* | (2011.01) |
| *H04N 5/30* | (2006.01) |
| *G01S 7/481* | (2006.01) |
| *G01S 17/89* | (2006.01) |
| *G02F 1/03* | (2006.01) |
| *G01N 21/3581* | (2014.01) |

(52) U.S. Cl.
CPC ............. *H04N 5/30* (2013.01); *G01N 21/3581* (2013.01); *G01S 7/4811* (2013.01); *G01S 17/89* (2013.01); *G02F 1/03* (2013.01); *G02F 2203/13* (2013.01)

(58) Field of Classification Search
CPC ........................................................ H04N 5/30
See application file for complete search history.

(56) References Cited

U.S. PATENT DOCUMENTS

| | | |
|---|---|---|
| 6,687,010 B1 | 2/2004 | Horii et al. |
| 2004/0109164 A1 | 6/2004 | Horii et al. |
| 2010/0090112 A1 | 4/2010 | Kawada et al. |

FOREIGN PATENT DOCUMENTS

| | | |
|---|---|---|
| JP | 11-142243 A | 5/1999 |
| JP | 2001-83077 A | 3/2001 |
| JP | 2008-096210 A | 4/2008 |
| WO | 2006/085403 A1 | 8/2006 |

OTHER PUBLICATIONS

Japanese Office Action dated Apr. 1, 2014, issued in Japanese Patent Application No. 2011-028349, w/partial English translation (4 pages).

*Primary Examiner* — Kate Luo
(74) *Attorney, Agent, or Firm* — Westerman, Hattori, Daniels & Adrian, LLP

(57) ABSTRACT

A first optical system irradiates a target with a detecting wave and making the detecting wave that is transmitted through the target incident upon the electrooptical crystal. A second optical system slants a pulse plane of a probe wave relative to a pulse plane of the detecting wave and making the probe wave incident upon the electrooptical crystal. A camera detects the probe wave passing through the electrooptical crystal. The first or second optical system includes a compensating component which partitions a beam cross section of the detecting wave or the probe wave into unit areas. The optical component makes different an optical path length of a beam passing each unit area and compensates a phase shifting between the pulse plane of the detecting wave and the pulse plane of the probe wave at positions in a crossing direction of a surface of the electrooptical crystal and the virtual plane.

8 Claims, 25 Drawing Sheets

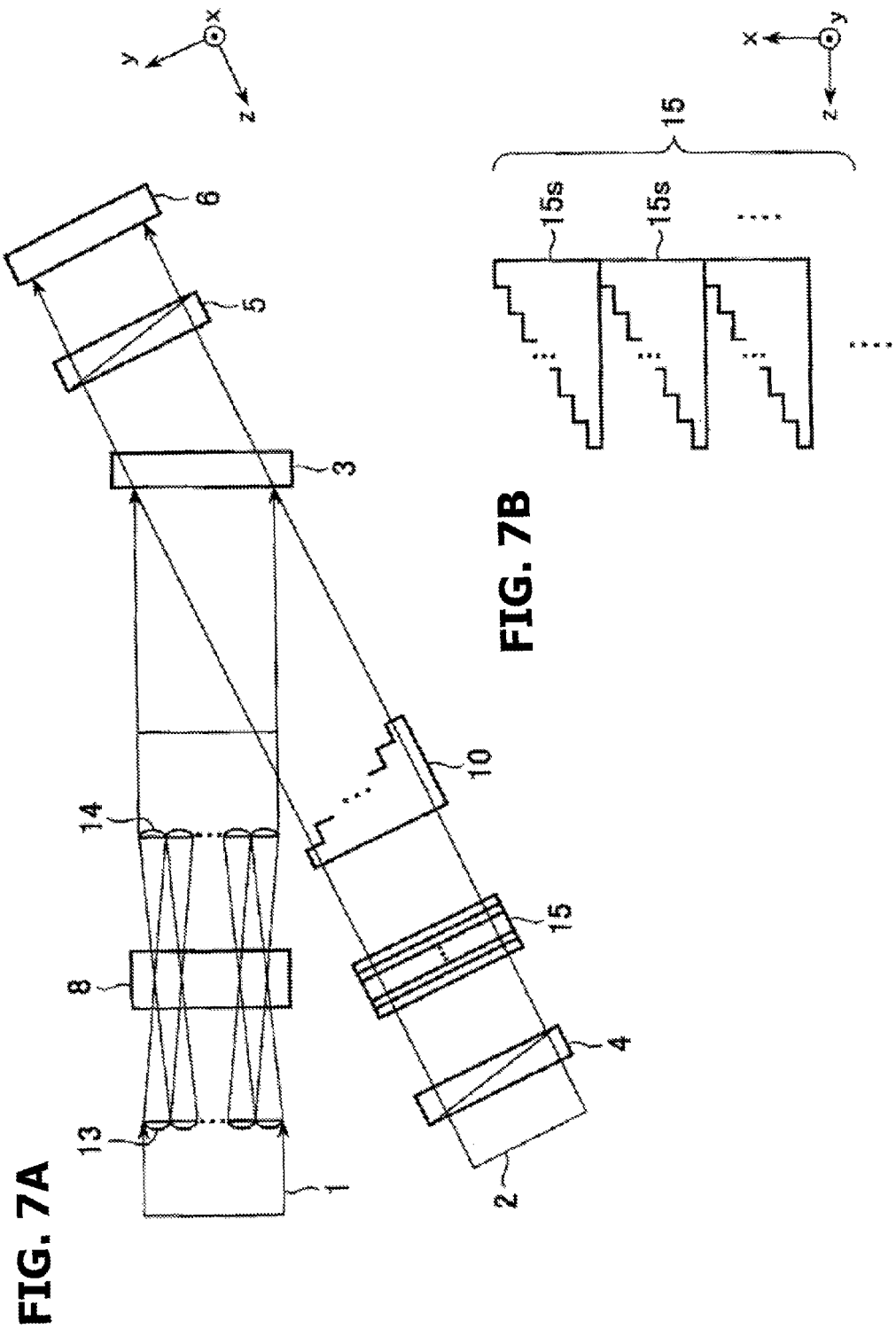

FIG. 14
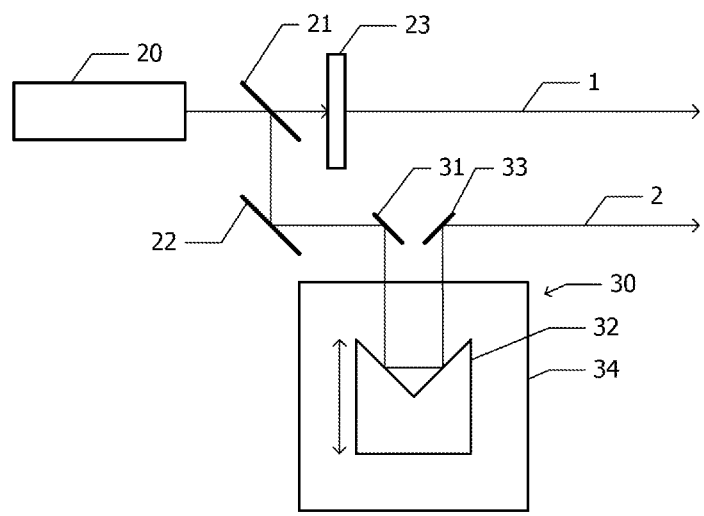
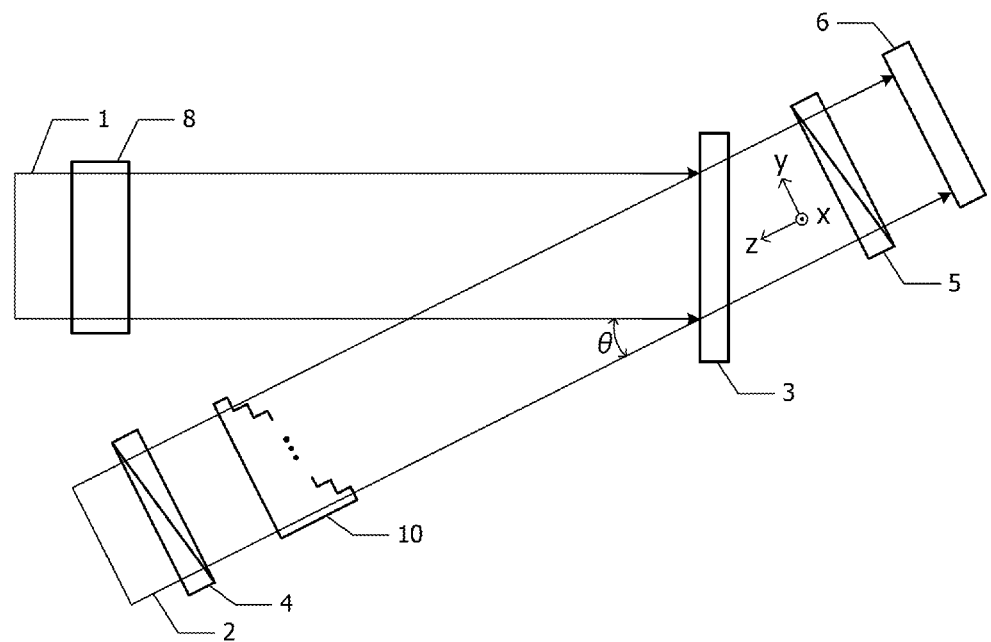

United States Patent US 9,204,063 B2

ELECTROMAGNETIC WAVE IMAGING APPARATUS

CROSS-REFERENCE TO RELATED APPLICATIONS

This application is based upon and claims the benefit of priority of the prior Japanese Patent Applications No. 2010-254404, filed on Nov. 15, 2010, and No. 2011-28349, filed on Feb. 14, 2011, the entire contents of which are incorporated herein by reference.

FIELD

The embodiments discussed herein are related to an electromagnetic imaging apparatus using two electromagnetic waves.

BACKGROUND

Various methods are known for observing an object by using electromagnetic waves, such as a method of obtaining data corresponding to an visual image by using visible light and a method of observing an invisible inner structure by using X-rays.

Terahertz waves are electromagnetic waves having a frequency range of 100 GHz to 10 THz and a wavelength range of 30 μm to 3 mm, which transmit through plastics, cloth, paper, semiconductor and the like, and have absorption spectra specific to substance. It is therefore possible to perform physicality analysis and inspection, radiographic imaging and the like. Applied techniques are also being developed. Optical terms such as an optical axis, a polarizer, an analyzer and the like may be used also in the terahertz wave wavelength range.

Since non-destructive composition analysis imaging is possible, this is expected as a composition analysis type inner radiographic imaging means as an alternative to a conventional inner radiographic imaging means (X-rays, ultrasounds and the like). Terahertz spectroscopic imaging has been proposed using characteristic THz absorption for measuring objects unable to be detected by conventional X-ray inspection, such as explosive substance (plastic bomb, flammable liquid and the like) in air port baggage inspection against recent terror and crime, prohibited substance (drug, antihypnotic agent and the like) in a sealed letter.

A method has been proposed wherein a pulse terahertz wave and a probe pulse light beam are input to an electrooptical (EO) crystal noncoaxially, an image by the probe pulse light beam is photographed with a digital camera, and a terahertz temporal waveform is measured in a single shot.

A method has also been proposed wherein a pulse terahertz wave and a probe pulse light beam are input to an electrooptical (EO) crystal coaxially. With this method, a plane (pulse plane) coupling peak positions of intensities of the probe pulse light beam is inclined relative to the pulse plane of the terahertz wave. By inclining one pulse plane relative to the other pulse plane, it becomes possible to obtain the same effects as those of the noncoaxial case.

PATENT DOCUMENT

International Publication Pamphlet No. WO 2006/085403
Japanese Laid-open Patent Publication No. 2008-96210

SUMMARY

In a method where a noncoaxicial optical system is used, detecting electromagnetic wave is condensed in a lineal region and irradiated to a measurement target, and imaging electromagnetic wave is used noncoaxically, scanning is required to obtain information with respect to a direction perpendicular to the lineal region. It becomes efficient if imaging at a plurality of positions is performed at the same time with respect to the direction perpendicular to the lineal region.

The embodiment discussed herein is related to an electromagnetic wave imaging apparatus including:

an electrooptical crystal;

a first optical system irradiating a measurement target with a pulsed detecting electromagnetic wave and making the electromagnetic wave that is transmitted through or reflected by the measurement target incident upon the electrooptical crystal;

a second optical system slanting a pulse plane of a pulsed probe wave for imaging relative to a pulse plane of the detecting electromagnetic wave and making the probe wave incident upon the electrooptical crystal; and, a camera detecting the probe wave passing through the electrooptical crystal, wherein the first optical system or the second optical system includes a compensating optical component which partitions a beam cross section of the detecting electromagnetic wave or the probe wave into a plurality of unit areas in a virtual plane perpendicular to a pulse plane of the detecting electromagnetic wave and to a pulse plane of the probe wave, the optical component making different an optical path length of a beam passing each unit area and compensating a phase shifting between the pulse plane of the detecting electromagnetic wave and the pulse plane of the probe wave at a plurality of positions in a crossing direction of a surface of the electrooptical crystal and the virtual plane.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIGS. 7A and 7B are cross sectional views illustrating a terahertz wave imaging apparatus of an embodiment 4, and a schematic cross sectional view illustrating the structure of an x-direction step-like transparent block 15 used in the embodiment 4.

FIG. 14 is a schematic diagram illustrating a terahertz wave imaging apparatus of an embodiment 6.

DESCRIPTION OF EMBODIMENTS

Prior to describing the embodiments, description will be made on the operation principle of a terahertz wave imaging apparatus which makes a terahertz wave and a probe wave noncoaxially incident upon an electrooptical crystal.

Figure 25:
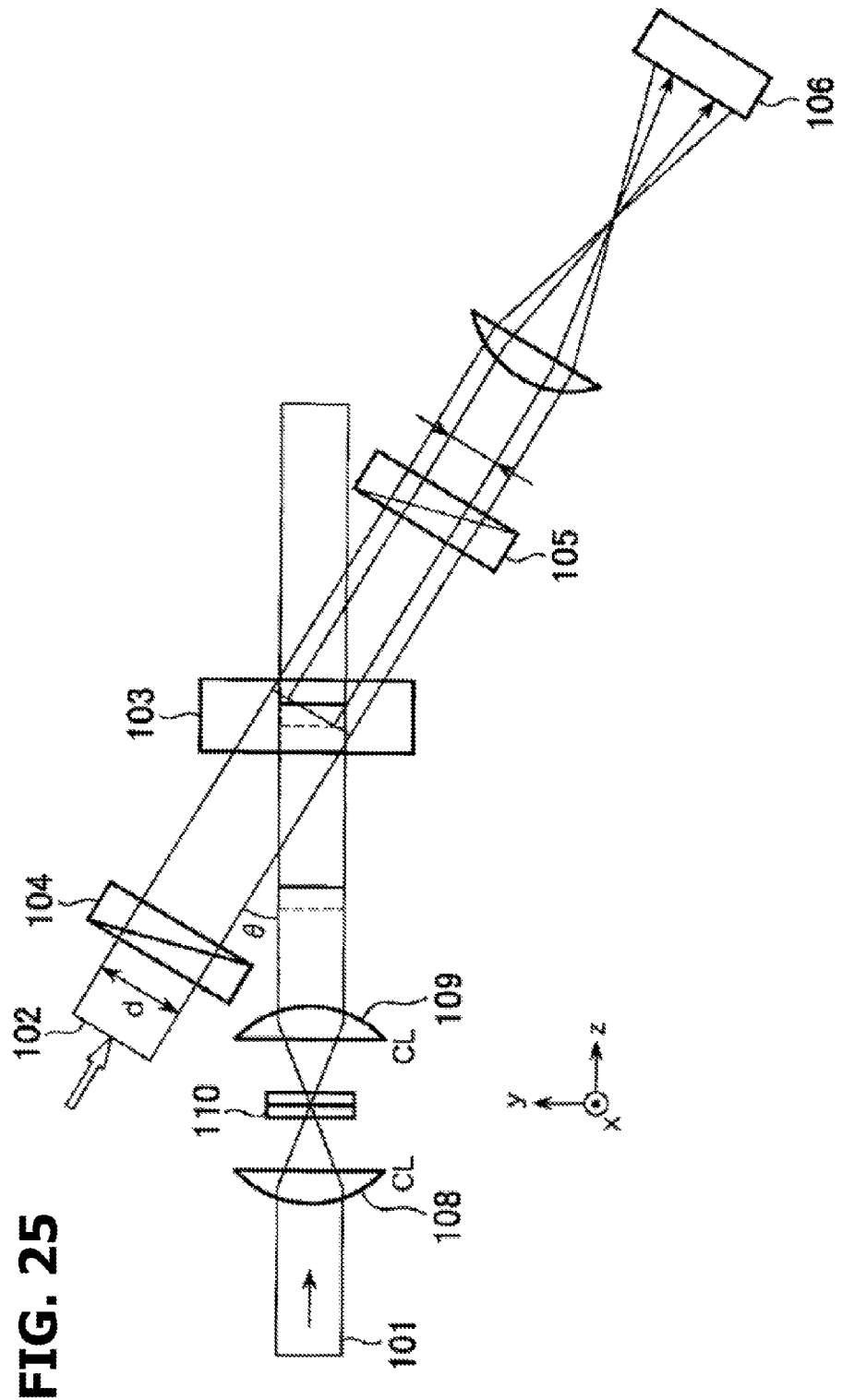
FIG. 25 is a diagram illustrating the principle of a real time terahertz wave imaging apparatus.

FIG. 25 is a diagram illustrating the operation principle of a terahertz wave imaging apparatus which makes a terahertz wave and a probe wave noncoaxially incident upon an electrooptical crystal. A pulse terahertz wave 101 propagating in a z-direction is condensed to a lineal region parallel to an x-axis by a cylindrical lens 108, and incident upon a measurement target 110. The pulse terahertz wave 101 obtains information on a lineal region along an x-axis direction of the measurement target 110. Instead of passing the pulse terahertz wave through the measurement target, it may be reflected on the measurement target. A parallel beam having a width in an x-y plane is recovered from the terahertz wave 101 passing through the lineal region of the measurement target 110 having a depth, by a cylindrical lens 109. Information on the lineal region in the x-axis direction is spread in the y-axis direction.

The pulse terahertz wave passing through the measurement target 110 is incident upon the electrooptical crystal 103. A birefringence change occurs in the electrooptical crystal 103 because of the electrooptical effect based on an electric field by the pulse terahertz wave 101 passing through the measurement target. A wave front (equiphase wave surface) indicated by a solid line advances in time from a wave front (equiphase wave surface) indicated by a broken line. The probe pulse wave 102 in noncoaxial alignment with the pulse terahertz wave 101 in the y-z plane is incident upon the electrooptical crystal 103. The pulse probe wave 102 is influenced in the electrooptical crystal 103 by the birefringence change caused by the pulse terahertz wave 101.

Because of noncoaxial alignment, there is a time difference between the timings when the wave fronts of the pulse terahertz wave 101 and the pulse probe wave 102 superpose, and a change in time appears in the y-axis direction. Namely, temporal change information of the lineal region in the x-axis direction is developed in the y-axis direction. A polarizer 104 and an analyzer 105 are cross Nichol arranged on the optical axis of the pulse probe wave sandwiching the electrooptical crystal 103. The pulse probe wave 102 influenced by the birefringence change caused by the pulse terahertz wave is picked up and measured with a CCD camera 106 including a focusing lens.

The wave front of the pulse probe wave 102 crosses the wave front of the pulse terahertz wave 101 at a cross angle θ. Focusing attention on the wave front of the pulse probe wave 102, when the upper side coincides with a solid line wave front of the pulse probe wave in FIG. 25, the lower side coincides with a broken line wave front of the pulse terahertz wave. Namely, time lapses from the upper side to the lower side.

The temporal change information developed in a propagation direction (z-axis direction) of the pulse terahertz wave 1 is developed in a direction perpendicular to one-dimensional image in the x-axis direction (in a beam width direction of the pulse prove wave 102) through temporospatial conversion in the electrooptical crystal 103. Information in a time-axis (depth) direction can be obtained by a two-dimensional imaging device. Similar to interference spectroscopy, it is possible to obtain spectra through Fourier transformation of the temporal information.

One axis of a two-dimensional image obtained with the two-dimensional imaging device is used for measuring a temporal waveform of the pulse terahertz wave, and the other axis is used for one-dimensional imaging (one-dimensional imaging in a two-dimensional plane) of the pulse terahertz wave passing in a lineal condensation (line beam) state. With respect to the y-axis direction in a real space, only one point can be measured. In order to obtain information in the y-axis direction, it is necessary to scan the lineal region, to which the pulse terahertz wave is condensed, in the y-axis direction. The present inventor has conceived that in-plane information is measured at the same time by dissolving a wave front.

Embodiment 1

Figure 1:
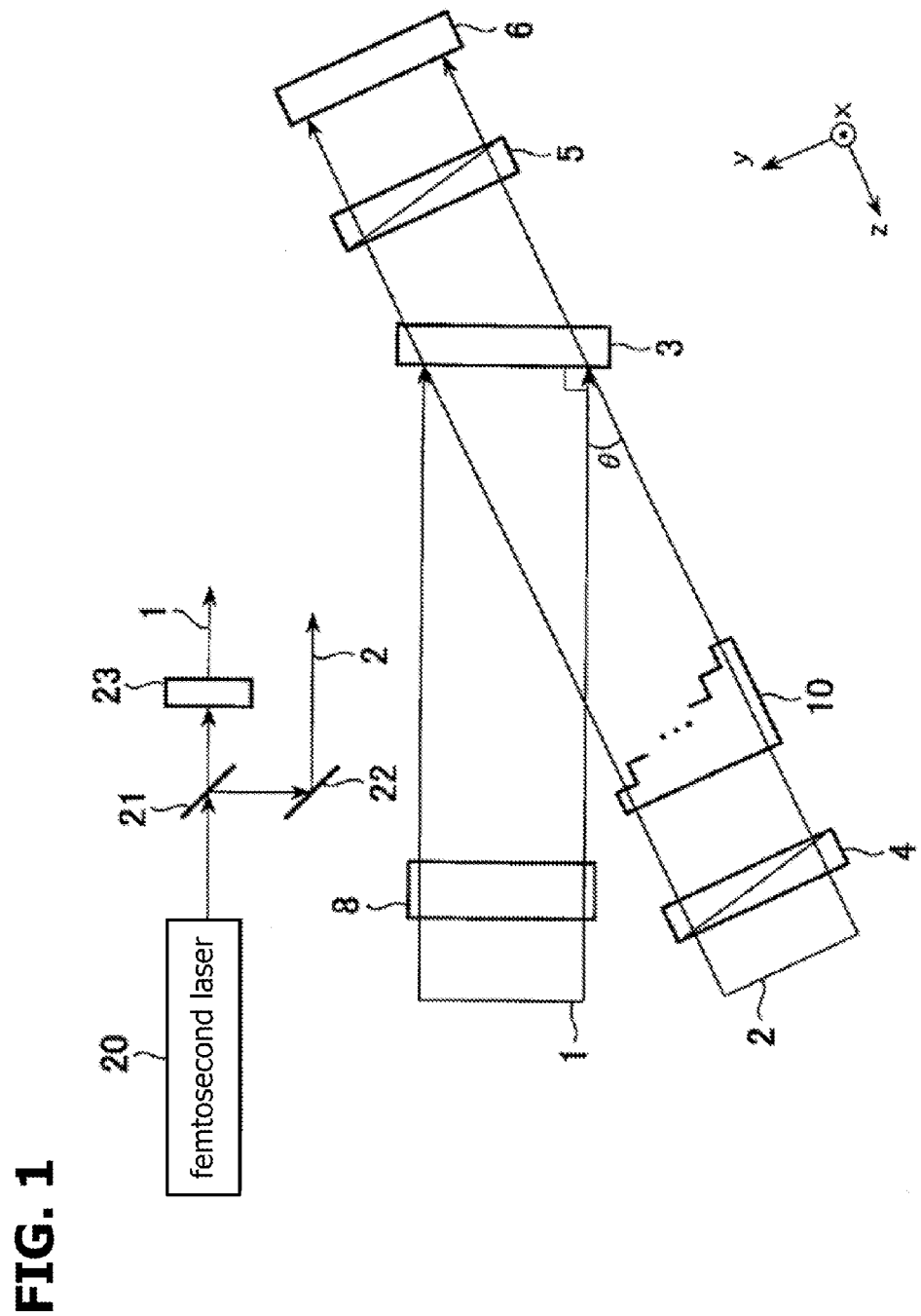
FIG. 1 is a schematic cross sectional view illustrating a terahertz wave imaging apparatus of an example 1 of an embodiment 1.

FIG. 1 is a schematic diagram illustrating an example 1 of a terahertz wave imaging apparatus of the embodiment 1. A terahertz wave 1 for detecting a measurement target and a probe wave 2 for imaging are incident upon an electrooptical crystal 3 noncoaxially. A digital camera 6 detects the probe wave 2 passing through the electrooptical crystal 3. An external air as an optical path of the terahertz wave 1 may be nitrogen atmosphere or vacuum if necessary.

A measurement target 8 is disposed on the optical path of the terahertz wave 1 that is collimated, and a transmitted light is vertically incident upon the electrooptical crystal 3. The wave front of the terahertz wave 1 is parallel to the surface of the electrooptical crystal 3. A collimated probe wave 2 is obliquely incident upon the electrooptical crystal 3 via a step-like transparent block 10 for forming an optical path difference (phase difference), at an incidence angle θ. Each tread face (terrace face) of the step-like transparent block 10 is vertical to a propagation direction of the probe wave 2 (parallel to wave front). The propagation direction of the probe wave 2 has an angle θ relative to the normal of the surface of the electrooptical crystal 3, and the wave fronts of the probe wave 2 and the terahertz wave 1 cross outside the electrooptical crystal 3 at an angle θ. A polarizer 4 and an analyzer 5 are cross Nichol arranged on the optical path of the probe wave 2 at a front side and a back side of the electrooptical crystal 3, respectively.

A birefringence change occurs in the electrooptical crystal 3 because of the electrooptical effect by an electric field of the terahertz wave 1 passing through the measurement target 8 and influenced by the measurement target 8. The linearly polarized probe wave 2 changes its polarization state (generally to elliptical polarization) because of the birefringence change of the electrooptical crystal 3. Only the change component of the polarization state of the probe wave 2 passes through the analyzer 5 and is input to the digital camera 6 including the focusing lens.

For example, as a common light source, a femtosecond laser 20 manufactured by Spectra-Physics Inc. and having a pulse energy of 1 mJ, a pulse width of 100 fs, a center wavelength of 800 nm, and a repetition frequency of 1 kHz. An output of the femtosecond laser 20 is branched into two beams by a beam splitter 21. One beam of them forms the probe wave 2, an optical path of which is adjusted by a mirror or the like if necessary. The other of the two beams is incident upon a terahertz wave generator unit using a ZnTe electrooptical crystal 23 to generate the pulse terahertz wave 1. A wavelength of the terahertz wave 1 spreads within a broad wavelength range. A time width of the pulse terahertz wave 1 falls within a range of 1 to 2 psec.

The electrooptical crystal 3 is made of, e.g., a 30 mm×30 mm×2 mm ZnTe crystal. The step-like transparent block 10 is made of, e.g., glass (BK7) having a refractive index of 1.51 at a wavelength of 800 nm. Other transparent materials may be used such as glass of other kinds, and organic resin that is transparent at a wavelength of 800 nm. The digital camera 6 is, e.g., a CCD camera including a focusing lens and having sensitivity at a wavelength of 800 nm, 512×512 pixels, and a pixel pitch of 20 μm. A magnification factor of the focusing lens is 0.3 in this case.

An x-y-z orthogonal coordinate system is defined in which a positive z-axis direction corresponds to a propagation direction of the probe wave 2, a width direction corresponds to the y-axis direction, a direction vertical to a drawing sheet (height direction) corresponds to the x-axis direction. The propagation directions of the terahertz wave 1 and the probe wave 2 are parallel to the y-z plane. Namely, a y-z plane is perpendicular to the wave fronts of the terahertz wave 1 and the probe wave 2. The wave fronts of the terahertz wave 1 and the probe wave 2 forms an angle θ in the y-z plane.

The collimated terahertz wave 1 is vertically incident upon the electrooptical crystal 3 via the measurement target 8. The collimated probe wave 2 propagates in the −z direction, and is obliquely incident upon the electrooptical crystal 3 at an incidence angle θ.

In this embodiment, the step-like transparent block 10 is disposed on the optical path of the probe wave 2 on the upstream side of the electrooptical crystal 3. The transparent block 10 has a refractive index higher than an external air having a refractive index of 1. In FIG. 1, the step-like transparent block 10 has a larger size (height) in the z-axis direction along the optical path, lowers stepwise along the y-axis direction, and the tread face (terrace face) parallel to the x-y plane extends in the x-axis direction. The beam cross section of the probe wave 2 is partitioned into a plurality of areas (unit areas) in the beam width direction, beams in the unit areas having optical path lengths different from each other. In one unit area, the optical path length is uniform. Specifically, the plurality of unit areas are defined in such a manner that the optical path length becomes stepwise longer toward the −y-direction.

Figure 2A:
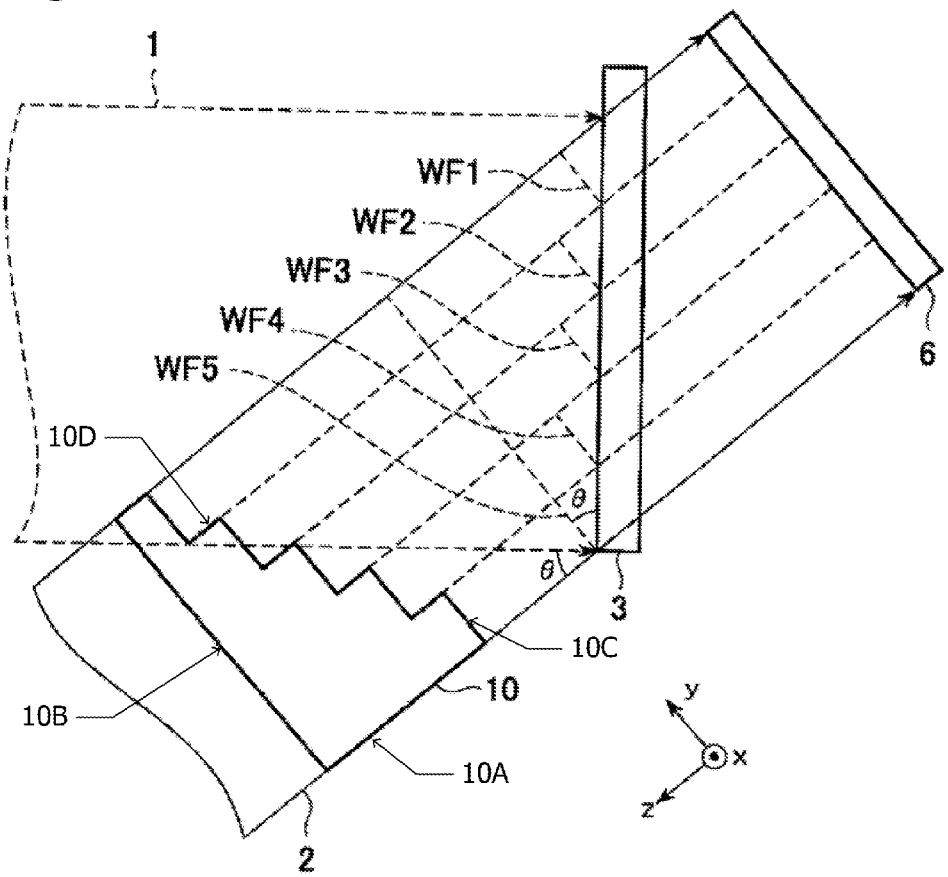
FIG. 2A is an enlarged cross sectional view illustrating the structure and function of a step-like transparent block 10.

FIG. 2A is an enlarged sectional view illustrating the structure and function of the step-like transparent block 10. The transparent block 10 has a surface 10A parallel to the x-z plane, a surface (bottom surface) 10B parallel to the x-y plane, and a tread faces 10C parallel to the x-y plane and opposite to the bottom surface 10B. The number of tread faces 10C is, e.g., five. A riser faces (step faces) 10D parallel to the x-z plane connects the tread faces 10C. Five unit areas having different optical path lengths are therefore defined in the beam cross section of the probe wave 2 in the beam width direction (y-axis direction).

A higher terrace face 10C (on the more negative side in the y-axis) the probe wave 2 passes, an optical path of the probe wave 2 becomes longer and the wave front delays more. Five wave fronts WF1 to WF5 are therefore formed. More positive side in the y-axis (upper side) the wave fronts WE1 to WF5 are disposed, the wave fronts become advanced. The surface of the electrooptical crystal 3 is inclined by an angle θ relative to the plane perpendicular to the propagation direction of the probe wave 2. Each step (a height of the riser face 10D) of the step-like transparent block 10 is designed so that the wave fronts WF1 to WF5 reach the electrooptical crystal 3 at the same time. The wave front of the terahertz wave 1 and the wave fronts of the probe wave 2 coincide (phase shift is compensated) at a plurality of positions (five positions) in the cross line direction between the surface of the electrooptical crystal 3 and the y-z plane.

FIG. 2A illustrates a state where the lower ends of the wave fronts WF1 to WF5 reach the electrooptical crystal 3 at the same time. As the wave fronts propagate, the upper ends of the wave fronts WF1 to WF5 gradually reach the electrooptical crystal 3. Namely, in each unit area, as described with reference to FIG. 25, the temporal information is developed in the y-axis direction. The information on the positions in the y-axis direction in the real space can be measured by the number of steps, in this case, five steps.

Figure 2B:
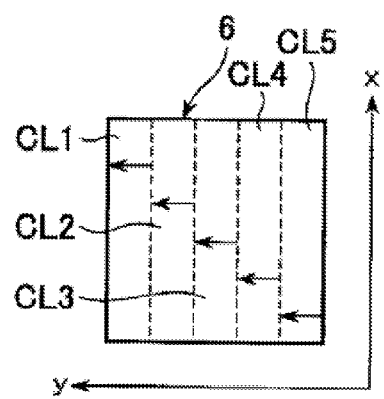
FIG. 2B is a plan view illustrating an area corresponding to the step-like transparent block 10 on an imaging plane of a digital camera 6.

FIG. 2B is a schematic diagram illustrating an imaging plane of the digital camera 6. The imaging plane is partitioned into five rectangular areas long in the x-direction corresponding to the unit areas partitioned by the step-like transparent block 10. Each rectangular area is called in some cases a cell CL1 to CL5. Ninety pixels are disposed in each cell in the width direction. The ninety pixels disposed in each cell in the width direction. The ninety pixels measure the temporal waveform of the terahertz wave 1.

Figure 3:
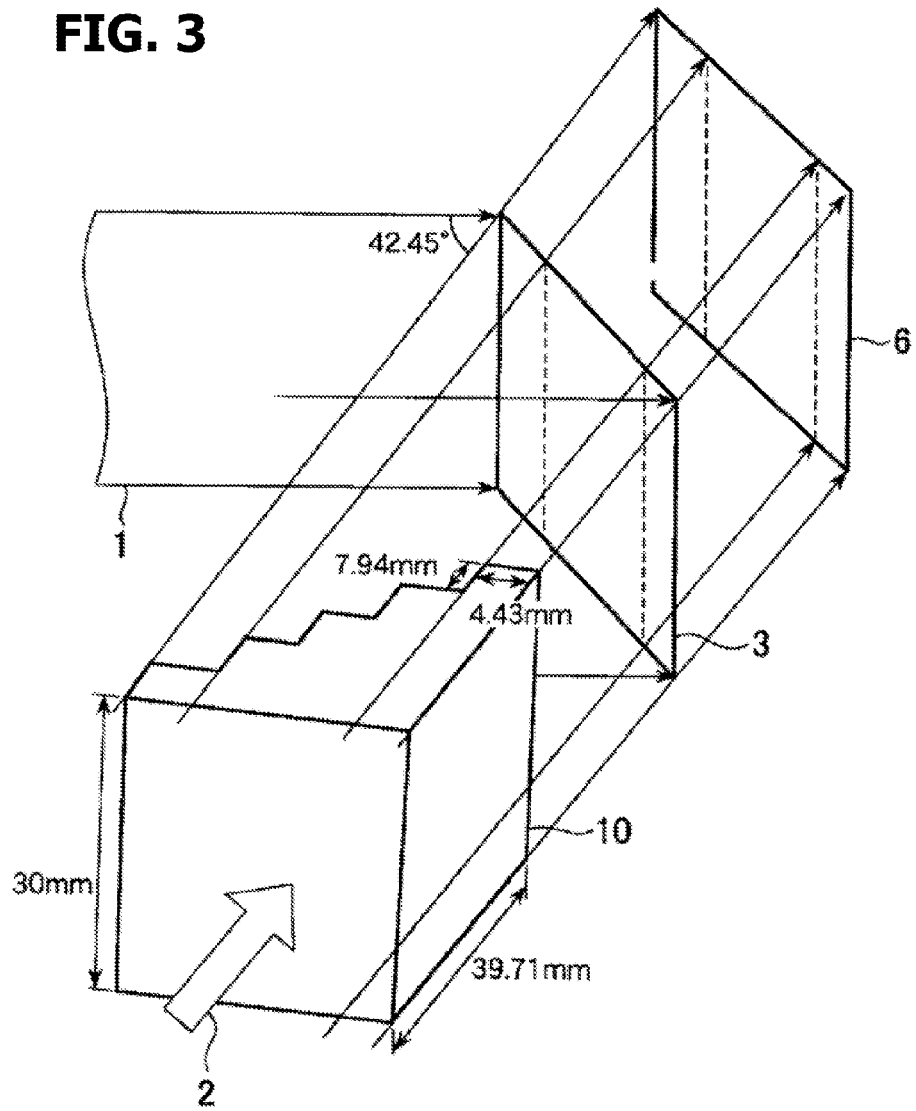
FIG. 3 is a perspective view illustrating an example of each size of the transparent block 10 used in the embodiment 1.

FIG. 3 is a perspective view illustrating a positional relation among the terahertz wave 1, the probe wave 2, the electrooptical crystal 3, the digital camera 6 and the step-like transparent block 10. The transparent block 10 for forming an optical path length difference for the probe wave 2 having a wavelength of 800 nm is made of glass (BK7). For spectroscopic imaging, the incidence angle θ of the probe wave 2 relative to the electrooptical crystal 3 is set to 42.45° to obtain a temporal waveform having a resolution performance of 0.15 psec and a time width of 13.5 psec and a spectrum having a resolution performance of 0.07 THz and a bandwidth of 3.33 THz. The glass transparent block 10 has a refractive index of 1.51, a lateral width of 22.13 mm, a height of 30 mm, and a height of the highest tread face from the bottom surface of 39.71 mm. A width of the terrace of each step parallel to the wave front is 4.43 mm, and a height of the riser face in the optical path direction is 7.94 mm. As the step-like transparent block 10 is disposed on the optical path of the probe wave 2 having a wavelength of 800 nm, it becomes possible to measure the temporal waveform of the terahertz wave 1 at five points disposed in a width direction of the measurement target 8 at the same time.

Figure 4:
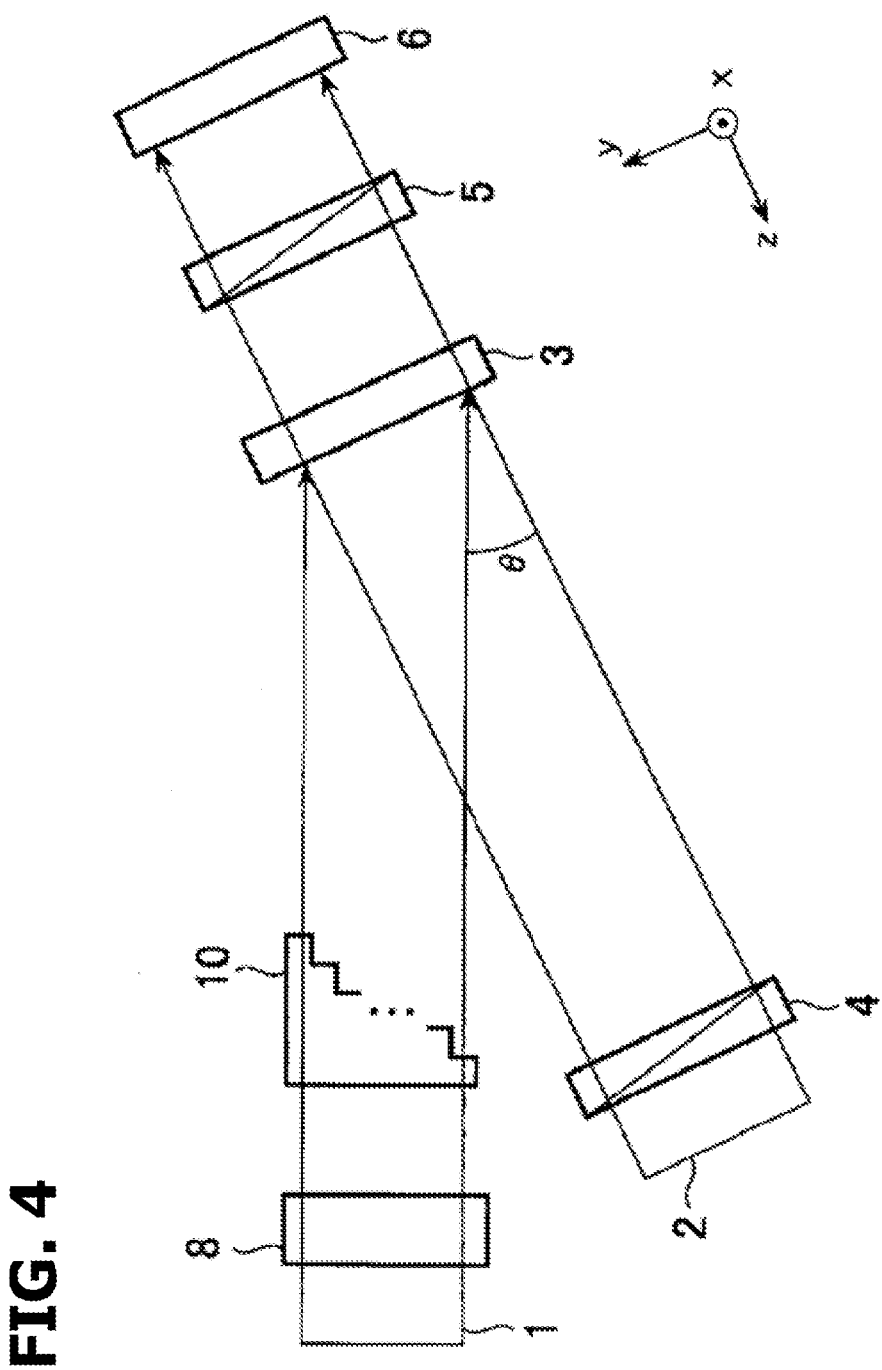
FIG. 4 is a schematic cross sectional view illustrating a terahertz wave imaging apparatus of an example 2 of the embodiment 1.

FIG. 4 illustrates an example 2 of the embodiment 1. In the example 2, the probe wave 2 is vertically incident upon the electrooptical crystal 3, and the terahertz wave 1 is obliquely incident upon the electrooptical crystal 3. The step-like transparent block 10 is disposed on the optical path of the terahertz wave 1 on the upstream side of the electrooptical crystal 3, in FIG. 4 between the measurement target 8 and the electrooptical crystal 3. Similar to the transparent block 10 of the example 1, the transparent block 10 has a function of giving an optical path length difference. However, the transparent block 10 is made of a transparent material in a wavelength band of the terahertz wave, e.g., polyethylene because the target wavelength is within a terahertz band. Other transparent materials may also be used such as diamond of type II, Si, Ge and the like.

The terahertz wave 1 is obliquely incident upon the electrooptical crystal 3 at an incidence angle θ, and in the state that the transparent block 10 is not disposed, the optical path length to the surface of the electrooptical crystal 3 is longer on the lower side in FIG. 4, and shorter on the upper side. In the step-like transparent block 10, a height from the bottom surface to the tread face is higher on the upper side, and lower on the lower side. A height of the tread face is designed so that the wave fronts of the terahertz wave 1 in a plurality of the unit areas reach the electrooptical crystal 3 at the same time. The wave front of the terahertz wave 1 passing through each unit area reaches the electrooptical crystal 3 faster on the upper side of each unit area, and the wave front on the lower side reaches the electrooptical crystal 3 with time. Similar to the example 1, the temporal information is developed in the width direction (y-axis direction) in each cell of the imaging plane of the digital camera 6.

Embodiment 2

Figure 5A:
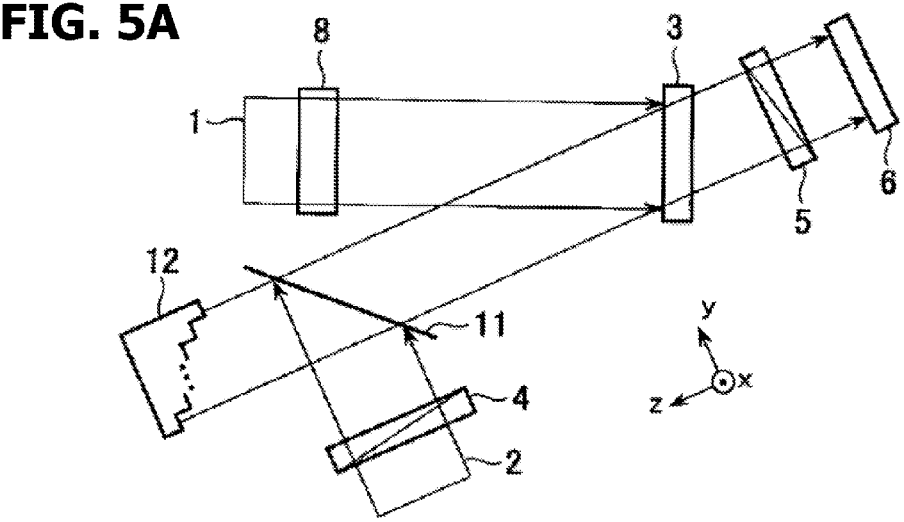
FIGS. 5A and 5B are cross sectional views illustrating a terahertz wave imaging apparatus of examples 1 and 2 of an embodiment 2.
Figure 5B:
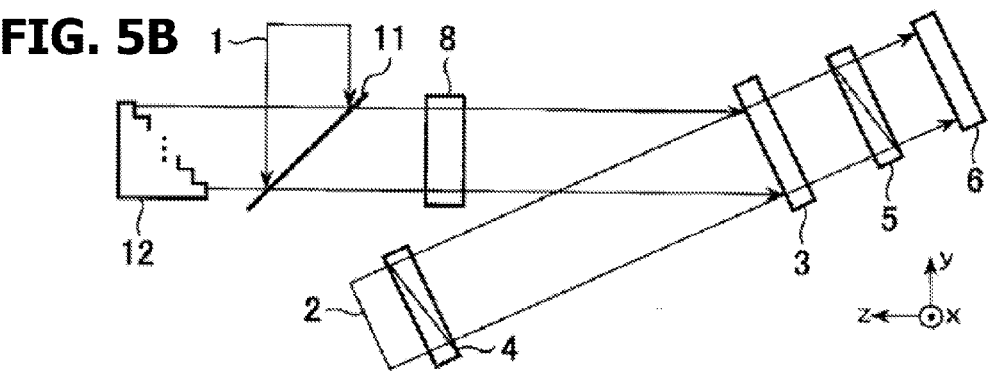

FIGS. 5A and 5B are cross sectional views illustrating the terahertz wave imaging apparatus of examples 1 and 2 of the embodiment 2. In the embodiment 1, the optical path difference (phase difference) is generated by disposing the step-like transparent block 10 on the optical path of the terahertz wave or the probe wave. In the embodiment 2, the electromagnetic wave is reflected at a step-like mirror to generate the optical path difference (phase difference). As an electromagnetic wave passes through the transparent block, some problems may occur, for example, the pulse width may be widened or the intensity may be attenuated. By using reflection at the mirror, it becomes possible to avoid the problems associated with passing through transparent material.

FIG. 5A illustrates the example 1 of the embodiment 2. Description will be made mainly on differences from the example 1 of the embodiment 1 illustrated in FIG. 1. In the example 1 of the embodiment 2, a beam splitter 11 and the step-like mirror 12 are disposed on the optical path of the probe wave 2. The step-like mirror 12 has a plurality of reflection planes at different positions in the propagation direction of the probe wave 2. The plurality of reflection planes partition a plurality of unit areas generating different optical path lengths. The optical system of the terahertz wave 1 is the same as that illustrated in FIG. 1. As compared with FIG. 1, the incidence optical path is changed by 90°.

The probe wave 2 passes through the polarizer 4, and thereafter is reflected at the beam splitter 11, and propagates away from the electrooptical crystal 3. Thereafter, the probe wave 2 is reflected by the step-like mirror 12, propagates along the same optical path in an opposite direction, passes through the beam splitter 11, and propagates toward the electrooptical crystal 3. As being reflected at each reflection plane of the step-like mirror 12, an optical path difference twice the height of the riser face of the step-like mirror 12 is given to the probe wave 2. The electrooptical crystal 3, the analyzer 5 and the digital camera 6 including the focusing lens are the same as those illustrated in FIG. 1.

The beam splitter 11 may be made of a half mirror. The half mirror for the probe wave having a wave length of 800 nm may be made of a thin film of reflexible metal such as Al, Ag, and Au, or a partial reflector (stripe) formed on a transparent material such as glass. The step-like mirror 12 may be made of a reflexible metal mirror formed on the surface of a structural body having a step-like surface. The material of the structural body is not limited specifically if it provides a physical support and forms a mirror surface.

FIG. 5B illustrates the example 2 of the embodiment 2. Description will be made mainly on differences from the example 2 of the embodiment 1 illustrated in FIG. 4. In the example 2 of the embodiment 2, the beam splitter 11 and step-like mirror 12 are disposed on the optical path of the terahertz wave 1. As compared with FIG. 4, the incidence optical path of the terahertz wave 1 is changed by 90°. As the terahertz wave reflected at the beam splitter 11 propagates toward the step-like mirror 12 and is reflected by the step-like mirror 12, the beam cross section of the terahertz wave 1 is partitioned into a plurality of unit areas generating different optical path lengths. The structure and function are the same as the beam splitter 11 and the step-like mirror 12 illustrated in FIG. 5A, excepting the operating wavelength. The beam splitter 11 may be made by forming a reflexible metal partial reflection mirror on a sheet made of transparent material such as polyethylene. The step-like mirror 12 may be made of a reflexible metal mirror formed on the surface of a structural body having a step surface. Other structures are the same as those illustrated in FIG. 4.

In the examples 1 and 2 of the embodiment 2, although there is no loss caused by the transmission through the transparent block, there is loss caused by the reflection at the beam splitter 11 and the transmission through the beam splitter 11. The beam splitter may be omitted.

Figure 5C:
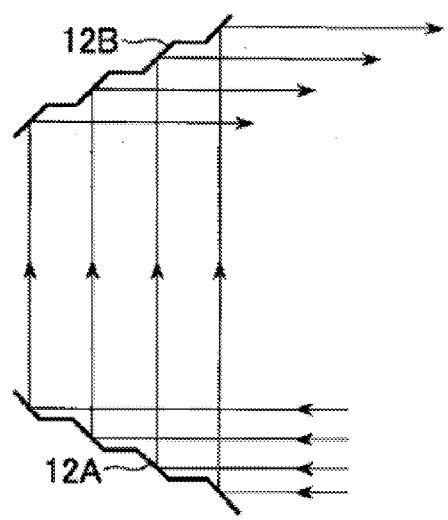
FIG. 5C is a cross sectional view illustrating an example 3 of the embodiment 2.

FIG. 5C illustrates an example 3 of the embodiment 2. The step-like mirrors 12A and 12B are used under an oblique incident condition without using the beam splitter. The riser face is made parallel to the incidence or reflection wave so that the riser face does not shade the beam. Description will be made assuming that an incidence angle to the reflection plane is 45°, and a change in a propagation direction of the electromagnetic wave is 90°. In the structure illustrated in FIG. 5C, the step-like mirror 12A has riser faces parallel to an incident wave, and the step-like mirror 12B has riser faces parallel to a reflected wave. A plurality of reflected wave fluxes reflected at a plurality of reflection planes of the step-like mirror 12A have gaps corresponding to depths (heights) of the riser faces. The gaps disappear in the plurality of reflected waves reflected at reflection planes of the step-like mirror 12B. A desired optical path difference (phase difference) is generated between a plurality of optical fluxes reflected at a plurality of reflection planes of the step-like mirrors 12A and 12B.

The step-like transparent block used in the embodiment 1 and the step-like mirror used in the embodiment 2 are considered that both compensate the timing (phase) shift between the terahertz wave (detecting electromagnetic wave) and the probe wave (imaging electromagnetic wave) on the surface of the electrooptical crystal, and may be called an optical compensating component.

Embodiment 3

Figure 6:
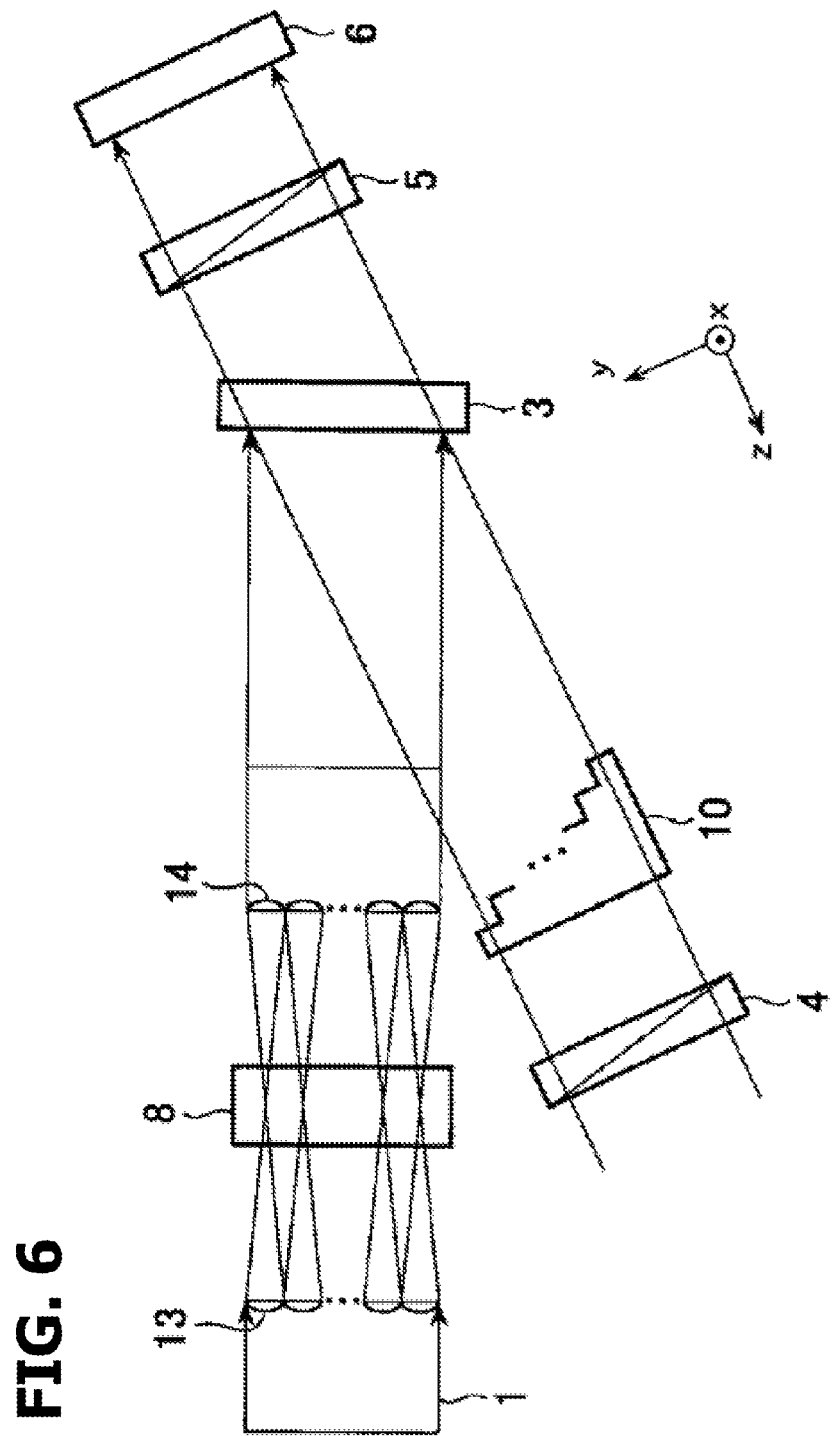
FIG. 6 is a cross sectional view illustrating a terahertz wave imaging apparatus of an embodiment 3.

FIG. 6 illustrates a terahertz wave imaging apparatus of the embodiment 3. In the embodiment 1, an electromagnetic wave passing through a spatial region in the measurement target 8 is incident upon each cell CL1 to CL5 (FIG. 2B). Information on different positions in the measurement target 8 is imaged at different positions in the y-axis (time axis) direction in each cell. In the embodiment 3, cylindrical lens arrays 13 and 14 are disposed front side and back side of the measurement target 8. The collimated terahertz wave 1 is condensed into a plurality of parallel lineal regions by the cylindrical lens array 13 and incident upon the measurement target 8, and the transmitted beam is recovered to a plurality of collimated light fluxes by the cylindrical lens array 14. Each collimated light flux spreads in a width direction, and is a terahertz wave passing through the lineal region of the measurement target 8. Any rays included in a light flux independent upon positions in the width direction have information on the same lineal region of the measurement target 8. The step-like transparent block 10 divides the probe wave 2 into a plurality of unit light fluxes having an optical path length difference. Each unit light flux of the probe wave 2 is incident upon the same region of the electrooptical crystal 3 as a corresponding collimated light flux of the terahertz wave 1. The number of lenses of each of the cylindrical lens arrays 13 and 14, the number of steps of the transparent block 10 and the number of cells of the digital camera are therefore the same. Noises are reduced by using the terahertz wave having the same information in the width direction of the cells.

The other structures are the same as the example 1 of the embodiment 1 illustrated in FIG. 1. As in the case of the example 2 of the embodiment 1, the probe wave 2 may be vertically incident upon the electrooptical crystal 3, the terahertz wave 1 may be obliquely incident upon the electrooptical crystal 3, and the step-like transparent block 10 may be disposed on the optical path of the terahertz wave 1.

Embodiment 4

FIGS. 7A and 7B illustrate a terahertz wave imaging apparatus of an example 1 of the embodiment 4. Description will be made mainly on different points from the embodiment 3 illustrated in FIG. 6. In the step-like transparent block 10 illustrated in FIG. 6, a size (a height from the bottom surface to the tread face) in the beam propagation direction of the probe wave 2 or terahertz wave 1 is different at each unit area (cell), and a plurality of tread faces extending in the x-axis direction are disposed in the y-axis direction (width direction). Constituent elements in FIG. 7A are all disposed in the same manner as illustrated in FIG. 6. Together with the step-like transparent block 10, another transparent block 15 is further disposed on the optical path of the probe wave 2.

The step-like transparent block 10 partitions the imaging plane (x-y plane) of the digital camera 6 into a plurality of cells CL1 to CL5 (FIG. 2B). In the embodiment 4, these cells are called "y-division cells".

FIG. 7B is a cross sectional view of the transparent block 15 perpendicular to the y-axis. The transparent block 15 includes a plurality of block elements 15s disposed in the x-direction and having the same shape. The block element 15s partitions the imaging plane into a plurality of x-division cells disposed in the x-direction. Each block element 15s has a flat bottom surface perpendicular to the z-axis, and a step-like surface constituted of riser faces perpendicular to the x-axis and tread faces perpendicular to the z-direction. Each tread face extends in the y-direction. The step-like surface lowers toward the positive direction of the x-axis with reference to the bottom surface perpendicular to the z-axis. Namely, a size of the probe wave in the propagation direction (z-direction) is different at each area (x-division cell) corresponding to the tread face, and an optical path length becomes shorter toward the positive direction in the x-axis.

The transparent block 10 having a different size in the z-direction dependent upon a position in the y-direction is called in some cases a y-direction step transparent block, and the transparent block 15 having a different size in the z-direction dependent upon a position in the x-direction is called in some cases an x-direction step transparent block.

The number of transparent block elements 15s is represented by $n_x$, and the number of steps of each transparent block element 15s is represented by $m_x$. The number of steps of a step-like y-direction transparent block 10 is represented by $n_y$.

Figure 8A:
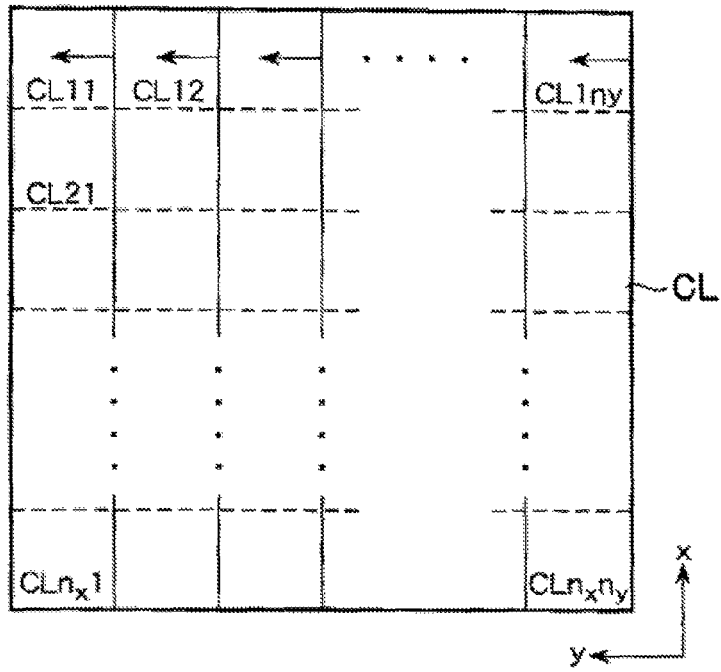
FIGS. 8A and 8B are schematic plan views illustrating image information on an imaging plane of the digital camera 6.
Figure 8B:
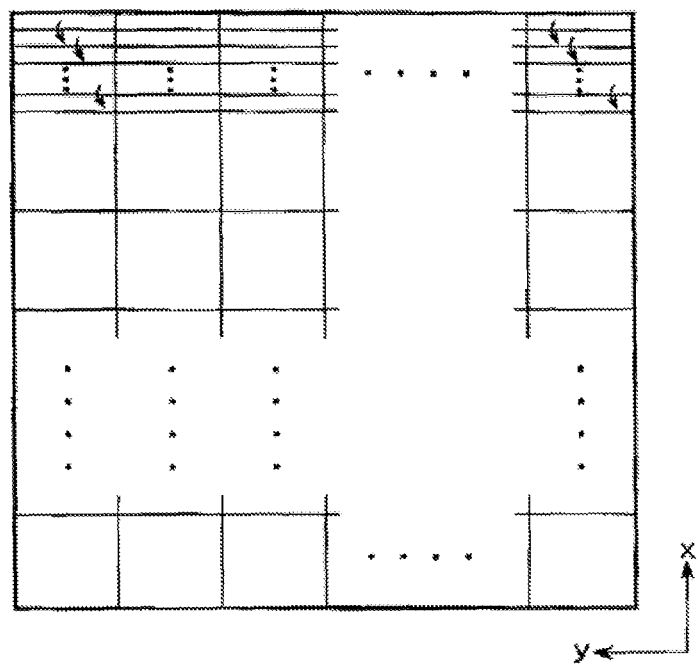

FIGS. 8A and 8B are schematic diagrams illustrating image information imaged on the imaging plane of the digital camera 6. As illustrated in FIG. 8A, $n_y$ steps of the y-direction step transparent block 10 form $n_y$ stripe areas (y-division cells) arranged in the y-direction. In each y-division cell, the wave front of the probe wave 2 reaches the electrooptical crystal 3 later from the right side (lower side in FIG. 7A) toward the left side. The x-direction step transparent block 15 has the structure that $n_x$ transparent block elements 15s are stacked in the x-direction, and divides the imaging plane into $n_x$ x-division cells in the x-direction.

One cell is defined by an area where the x-division cell extending in the y-direction crosses the y-division cell extending in the x-direction. In the imaging plane, ($n_x \times n_y$) cells CL are defined. An m-th cell at an n-th row is represented by CLnm. The upper left cell is represented by CL11, and the lower right cell is represented by $CLn_xn_y$. Each transparent block element 15s has $m_x$ tread faces arranged in the x-direction.

As illustrated in FIG. 8B, corresponding to the tread face of the transparent block element 15s, each cell CL is divided into $m_x$ areas (sub areas) in the x-direction. The probe wave 2 incident upon the $m_x$ sub areas has an optical path length that varies by each sub area. In the structure illustrated in FIG. 7B, the probe wave passes through the tread face positioned in the more positive direction in the x-axis, shorter the optical path length of the probe wave becomes. The wave front of the probe wave passes through the tread face positioned in the more positive direction in the x-axis, earlier the wave front reaches the electrooptical crystal. By adjusting the timing difference caused by an optical path length difference, it becomes possible to adjust scan timings of each sub area so that a scan in the first sub area is followed by a scan in the second sub area, and the scan in the second sub area is followed by a scan in the third sub area and so on in each cell CL. Waveform information of the terahertz wave is therefore elongated by $m_x$ times on the time axis.

An example of each parameter will be described. A size of the electrooptical crystal 3 is 30 mm×30 mm×2 mm. A magnification factor of the focusing lens of the digital camera 6 is 0.3, the number of pixels is 512×512, and a pixel pitch is 20 μm. A temporal waveform having a resolution power Td of 0.1 psec and a time width Tw of 25.6 psec and a spectrum having a resolution power of 0.04 THz and a band width of 5 THz are obtained. The number $n_y$ of steps of the y-direction step transparent block 10 is 14. The number $n_x$ of transparent block elements 15s constituting the x-direction step transparent block 15 is 14, and the number $m_x$ of steps of each transparent block element 15s is 8.

The number of pixels of each cell CL is 32×32. One tread face of the transparent block element 15s has a width corresponding to four pixels. An incidence angle θ of the probe wave 2 into the electrooptical crystal 3 is 26.62°. The transparent blocks 10 and 15 are made of glass having a refractive index of 1.51. A width (size in the y-direction), a size in the z-direction, and a size in the x-direction of the y-direction step transparent block 10 are, 26.82 mm, 26.35 mm and 30 mm, respectively. A width (size in the y-direction) of each tread face is 1.92 mm, and a height (size in the z-direction) of each riser face is 1.88 mm. A width (size in the y-direction), a size in the z-direction, and a size in the x-direction of each of the transparent block elements 15s are, 26.82 mm, 15.06 mm and 30 mm, respectively. A width (size in the x-direction) of each tread face of the transparent block element 15s is 0.27 mm, and a height (size in the z-direction) of each tread riser face is 1.88 mm.

The wave front of the probe wave 2 reaches the electrooptical crystal 3 at the same time with respect to the x-direction. The x-direction step transparent block 15 generates a time difference with respect to the x-direction originally having no time difference. The direction of increasing or decreasing the optical path length in the x-direction may be reversed.

In the embodiment 4 wherein the terahertz wave 1 is vertically incident upon the electrooptical crystal 3, the x-direction step transparent block 15 is disposed to generate an optical path length difference in the x-direction. As in the example 2 of the embodiment 1 illustrated in FIG. 4, a similar x-direction step transparent block may be disposed on the optical path of the terahertz wave 1, if the probe wave 2 is vertically incident upon the electrooptical crystal 3. The y-direction step transparent block 10 and the x-direction step transparent block 15 may be disposed on different optical paths.

Figure 9:
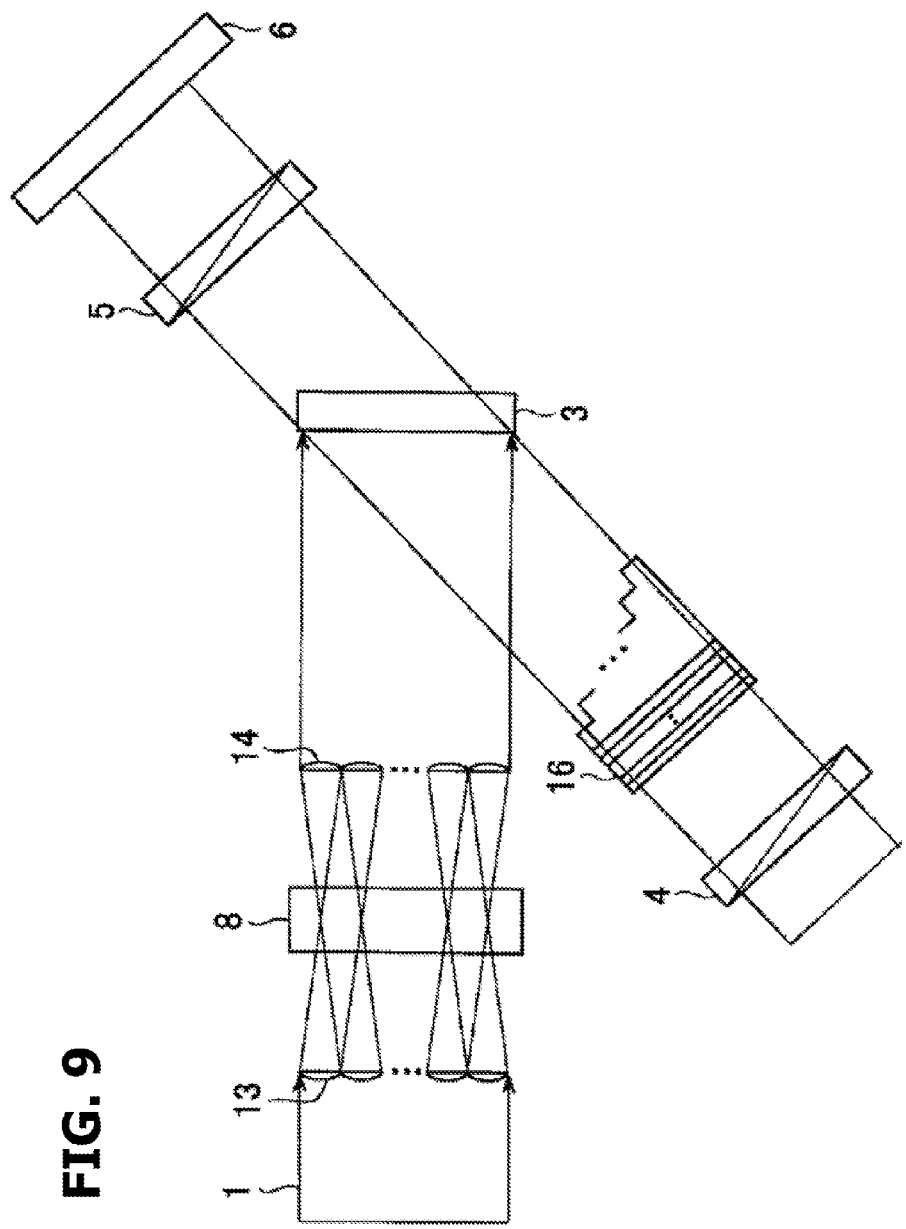
FIG. 9 is a cross sectional view illustrating a terahertz wave imaging apparatus of a modification of the embodiment 4.

FIG. 9 illustrates a terahertz wave imaging apparatus of an example 2 of the embodiment 4. The y-direction step transparent block 10 and the x-direction step transparent block 15 illustrated in FIG. 7A are combined to form a y-direction x-direction step transparent block 16. In this example, although the transparent block is disposed on the optical path of the probe wave 2, a similar modification is possible also for the example in which the transparent blocks are disposed on the optical path of the terahertz wave 1.

Embodiment 5

Figure 10:
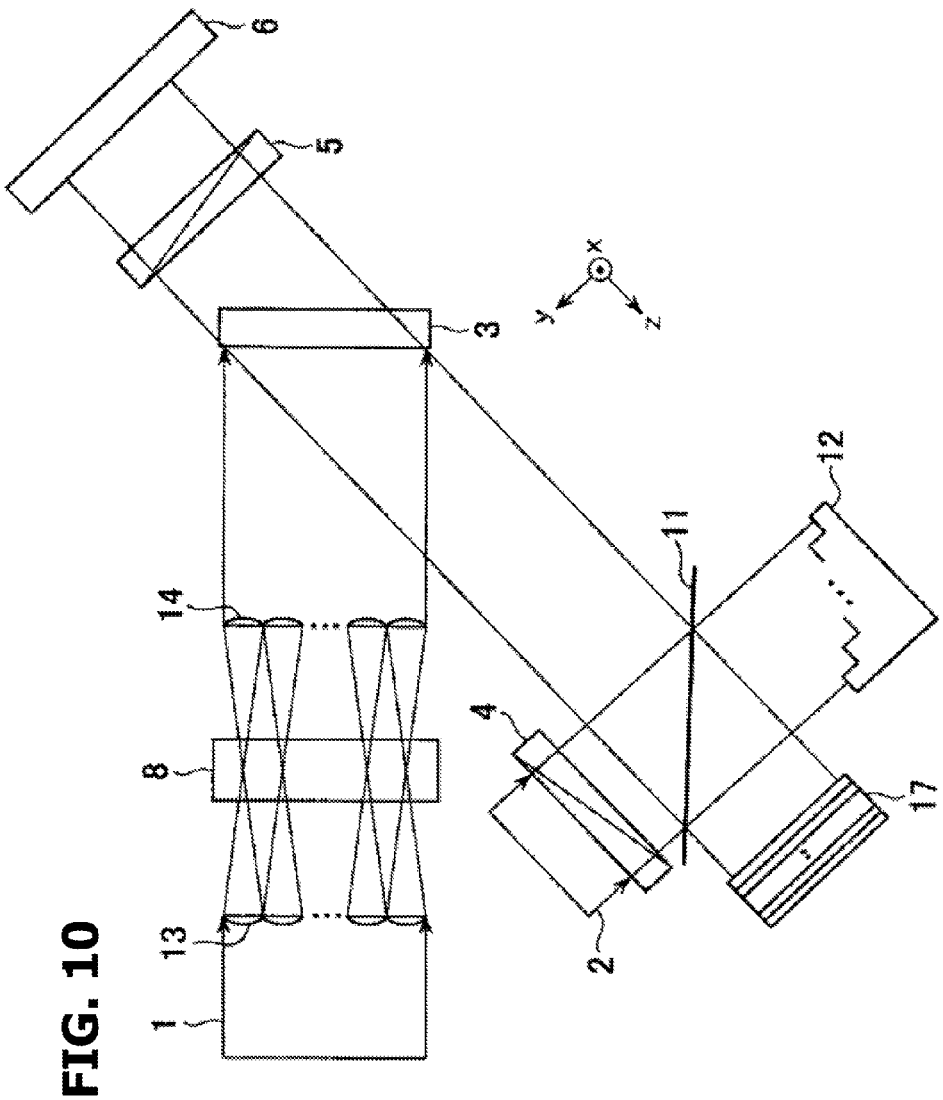
FIG. 10 is a cross sectional view illustrating a terahertz wave imaging apparatus of an embodiment 5.

FIG. 10 illustrates a terahertz wave imaging apparatus of the embodiment 5. The whole optical path of the terahertz wave 1 and the structure lying downstream of the electrooptical crystal 3 are the same as the embodiment 3 illustrated in FIG. 6. In the embodiment 5, the probe wave 2 that passed through the polarizer 4 passes through the beam splitter 11, and is incident upon a width direction (y-direction) step-like mirror 12. A reflected beam from the width direction step-like mirror 12 is reflected at the beam splitter 11 and incident upon the height direction (x-direction) step-like mirror array 17. A reflected beam from the x-direction step-like mirror array 17 passes through the beam splitter 11 and is obliquely incident upon the electrooptical crystal 3. The height direction (x-direction) step-like mirror array 17 is formed by forming a mirror on the step surface of the underlying structure having a shape similar to the x-direction step transparent block 15 stacking the transparent block elements 15s illustrated in FIG. 7B.

In FIG. 10, a propagation direction of the probe wave 2 at the position where the width direction step-like mirror 12 is disposed is displaced from the axis direction of the probe wave 2 at the position where the electrooptical crystal 3 is disposed. However, basing upon the xyz coordinate system at the position where the electrooptical crystal 3 is disposed, the width direction step-like mirror 12 is called a y-direction step-like mirror. The height direction step-like mirror array 17 is called an x-direction step-like mirror array. The probe wave 2 is divided into a plurality of unit beams having different optical path lengths and arranged in the y-direction by the y-direction step-like mirror 12, and is divided into a plurality of unit beams having different optical path lengths and arranged in the x-direction by the x-direction step-like mirror array 17. Although the refractive index of the medium in the area where the probe wave 2 passes is 1, the probe wave 2 reciprocates the path where the optical path difference is generated so that the step effect is doubled. If the same characteristics as those of the structure illustrated in FIGS. 8A and 8B are to be obtained, a height from the bottom surface of the y-direction step-like mirror 12 to the highest tread face is 6.72 mm, and a step (height of each riser face) is 0.48 mm. A height from the bottom surface of the x-direction step-like mirror array 17 to the highest tread face is 3.84 mm, and a step (height of each riser face) is 0.48 mm. Other dimensions do not change.

FIG. 10 illustrates the example in which the step-like mirror is disposed on the optical path of the probe wave. The step-like mirror may be disposed on the optical path of the terahertz wave. The y-direction step-like mirror and the x-direction step-like mirror array may be disposed on different optical paths.

Figures 11A, 11B:
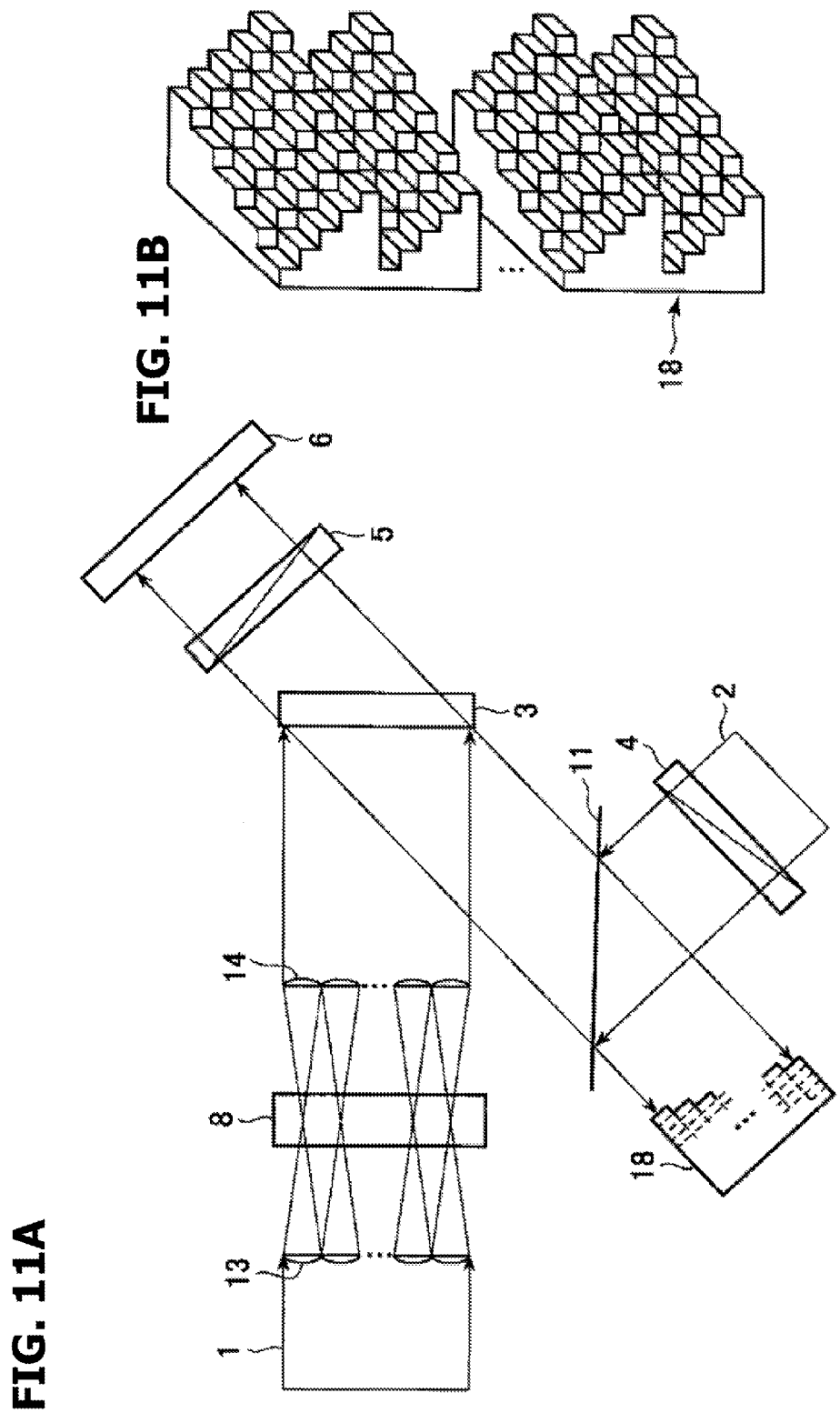
FIGS. 11A and 11B are cross sectional views illustrating a terahertz wave imaging apparatus of a modification of the embodiment 5, and a schematic perspective view illustrating the structure of a y-direction and x-direction step-like mirror array.

FIGS. 11A and 11B illustrate a terahertz wave imaging apparatus of a modification of the embodiment 5. FIG. 11A illustrates the structure of a y-direction x-direction step-like mirror array 18 which is obtained by combining the y-direction step-like mirror 12 and the x-direction step-like mirror array 17 illustrated in FIG. 10.

FIG. 11B is a schematic perspective view illustrating the structure of the y-direction x-direction step-like mirror array 18. Reflection plane has steps in y-direction and x-direction.

As the two mirrors are combined, an optical path is simplified. The probe wave 2 that passed through the polarizer 4 is reflected at the beam splitter 11 and incident upon the y-direction x-direction step-like mirror array 18. Reflected beam from the y-direction x-direction step-like mirror array 18 passes through the beam splitter 11, and is incident upon the electrooptical crystal 3. Other structures are the same as those of the embodiment 5 illustrated in FIG. 10.

Figure 12:
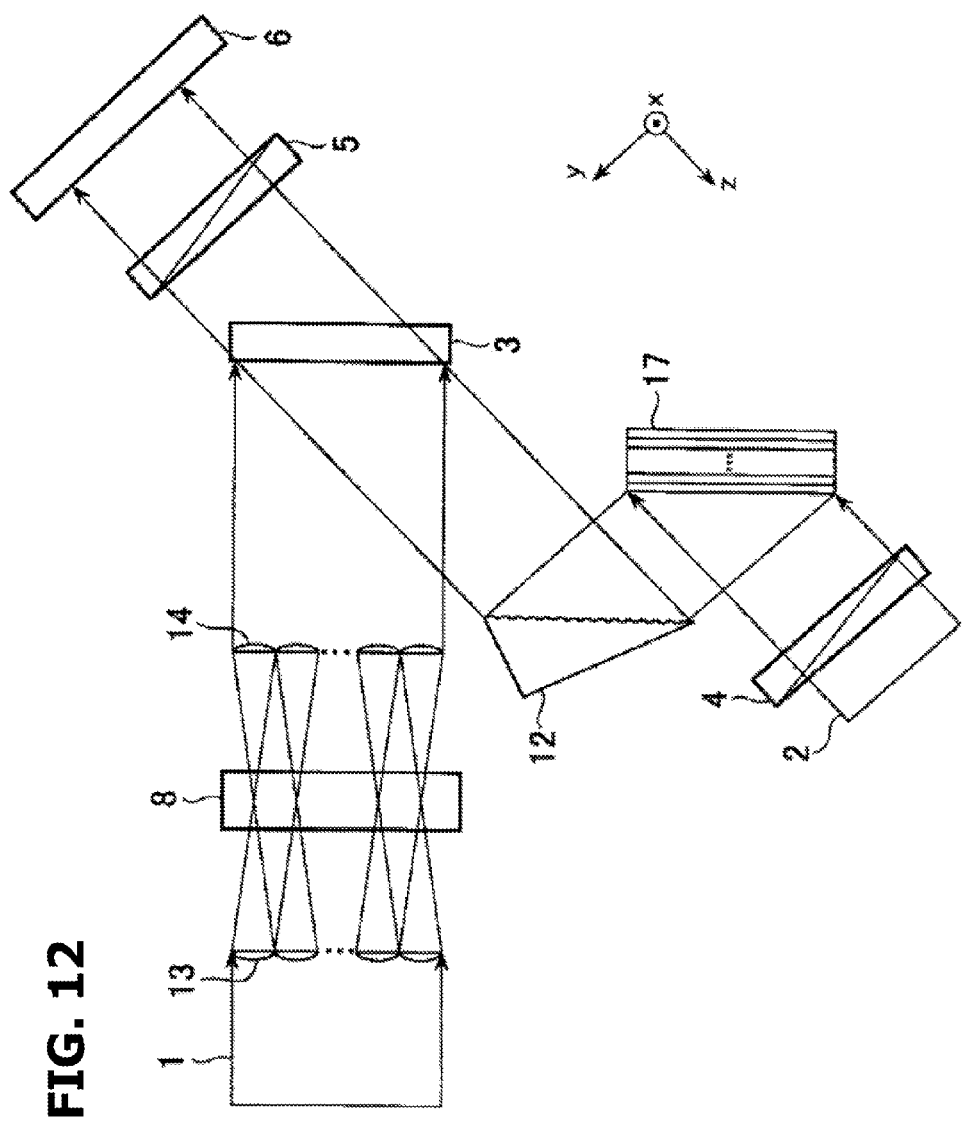
FIG. 12 is a cross sectional view illustrating a terahertz wave imaging apparatus of another modification of the embodiment 5.

FIG. 12 illustrates a terahertz wave imaging apparatus of a further modification of the embodiment 5. As compared to the structure illustrated in FIG. 10, the beam splitter 11 is omitted. The probe wave 2 is obliquely incident upon the x-direction step-like mirror array 17 at an incidence angle of 45°. The probe wave 2 reflected from the x-direction step-like mirror array 17 is obliquely incident upon the y-direction step-like mirror 12 at an incidence angle of 45°.

Figure 13A:
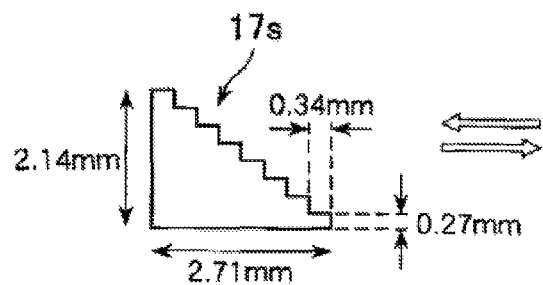
FIGS. 13A and 13B are cross sectional views illustrating one unit of an x-direction step-like mirror array 17 to be used in another modification of the embodiment 5 illustrated in FIG. 12 and an example of a y-direction step-like mirror 12.
Figure 13B:
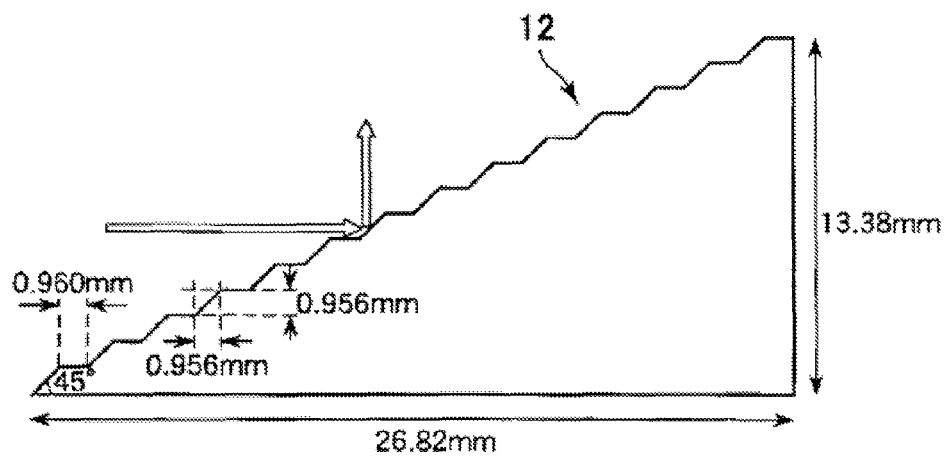

FIGS. 13A and 13B illustrate one unit 17s of the x-direction step-like mirror array 17 and an example of the shape of the y-direction step-like mirror 12. The step (riser face) of the x-direction step-like mirror 17s is parallel to the y-z plane and to the incidence light. In the x-direction step-like mirror 17s, an angle between the riser face and the tread face is 90°. The reflection plane (tread face) has a stripe shape that is long in a direction perpendicular to the drawing sheet, and even if light is incident obliquely in the length direction, the light will not be shaded.

In the y-direction step-like mirror 12 illustrated in FIG. 13B, steps (riser faces) parallel to the incident light couple a plurality of reflection planes (tread faces) whose normal has an angle of 45° with respect to the incident light.

For example, by using the electrooptical crystal of 30 mm×30 mm×2 mm and a digital camera having a focusing lens magnification factor of which is 0.3, the number of pixels of 512×512 and a pixel pitch of 20 μm, two-dimensional imaging is performed for a measurement target of the terahertz wave. The x-direction step-like mirror array 17 is constituted of fourteen x-direction step-like mirrors 17s, and each x-direction step-like mirror 17s has eight reflection planes (tread faces). The y-direction step-like mirror 12 has fourteen reflection planes (tread faces). It is assumed that each cell includes 16×16 pixels.

It is considered to obtain a temporal waveform having a resolution power Td of 0.1 psec and a time width Tw of 12.8 psec and a spectrum having a resolution power of 0.08 THz and a band width of 5 THz. An incidence angle θ of the probe wave 2 to the electrooptical crystal 3 is 26.62°. A width of a plane perpendicular to an incident light, a width of a plane perpendicular to an outgoing light and a height of the y-direction step-like mirror 12 are 13.38 mm, 26.82 mm and 30 mm, respectively. A width of an incident light to each reflection plane (tread face) and a width of an outgoing light from each reflection plane (tread face) are both 0.956 mm. A size (height) of the back surface of each x-direction step-like mirror 17s is 2.14 mm. A width of a reflection plane (tread face) is 0.27 mm, a step (height of riser face) is 0.34 mm. A size of the x-direction step-like mirror array 17 having fourteen x-direction step-like mirrors 17s which are arranged is 22.76 mm×2.71 mm×30 mm.

In the y-direction step-like mirror 12 illustrated in FIG. 13B, there is a gap between reflected beams reflected at adjacent reflection planes. It is possible to prevent the gap from being generated by forming an optical path length different by combining two mirrors as illustrated in FIG. 5C.

It is possible to consider that the x-direction step-like transparent block and the x-direction step-like mirror array used in the embodiments 4 and 5 are to be an optical element for dividing beams having the same phase in the beam cross section into a plurality of unit beams having phases different from each other. It is therefore possible to call the x-direction step transparent block and x-direction step-like mirror array as a phase shifting optical component.

Embodiment 6

The embodiment 6 will be described with reference to FIGS. 14 to 16. In the embodiment 1, a measurable time width is limited as illustrated in FIG. 2A by the time from when the lower end of each of the wave fronts WF1 to WF5 of the probe wave 2 reaches the electrooptical crystal 3 to when the upper end of each of the wave fronts WF1 to WF5 of the probe wave 2 reaches the electrooptical crystal 3. In the embodiment 6, it is possible to widen a measurable time width.

FIG. 14 is a schematic diagram illustrating an electro magnetic wave imaging apparatus of the embodiment 6. Description will be made mainly on different points from the example 1 of the embodiment 1. In the embodiment 6, a time delay unit 30 is disposed on the optical path of the probe wave 2. The time delay unit 30 includes mirrors 31 and 33, a movable mirror 32 and a linear motion stage 34. The movable mirror 32 has two reflection planes (first and second reflection planes) crossing perpendicularly with each other.

The probe wave 2 that was reflected by the mirror 22 is reflected by the mirror 31 and incident upon the first reflection plane of the movable mirror 32 at an incident angle of 45°. The probe wave 2 that was reflected by the first reflection plane is incident upon the second reflection plane at an incident angle of 45°. The probe wave 2 that was reflected by the second reflection plane is reflected by the mirror 33 and propagates toward the analyzer 4.

The linear motion stage 34 moves the movable mirror 32 in a direction parallel to a propagation direction of the probe wave 2 incident upon the first reflection plane (a propagation direction of the probe wave 2 reflected at the second reflection plane). It is possible to change a delay time of the probe wave 2 relative to the terahertz wave 1 by adjusting the optical path length from the mirror 31 to the first reflection plane of the movable mirror 32.

An optical path of the terahertz wave 1 and an optical path of the probe wave 2 after passing through the time delay unit 30 are the same as those of the embodiment 1.

Description will now be made on the imaging method of the electromagnetic wave imaging apparatus of the embodiment 6. As in the case of the embodiment 1 illustrated in FIG. 1, it is possible to measure temporal waveforms of the terahertz wave 1 by fixing the position of the movable mirror 32.

Figure 15:
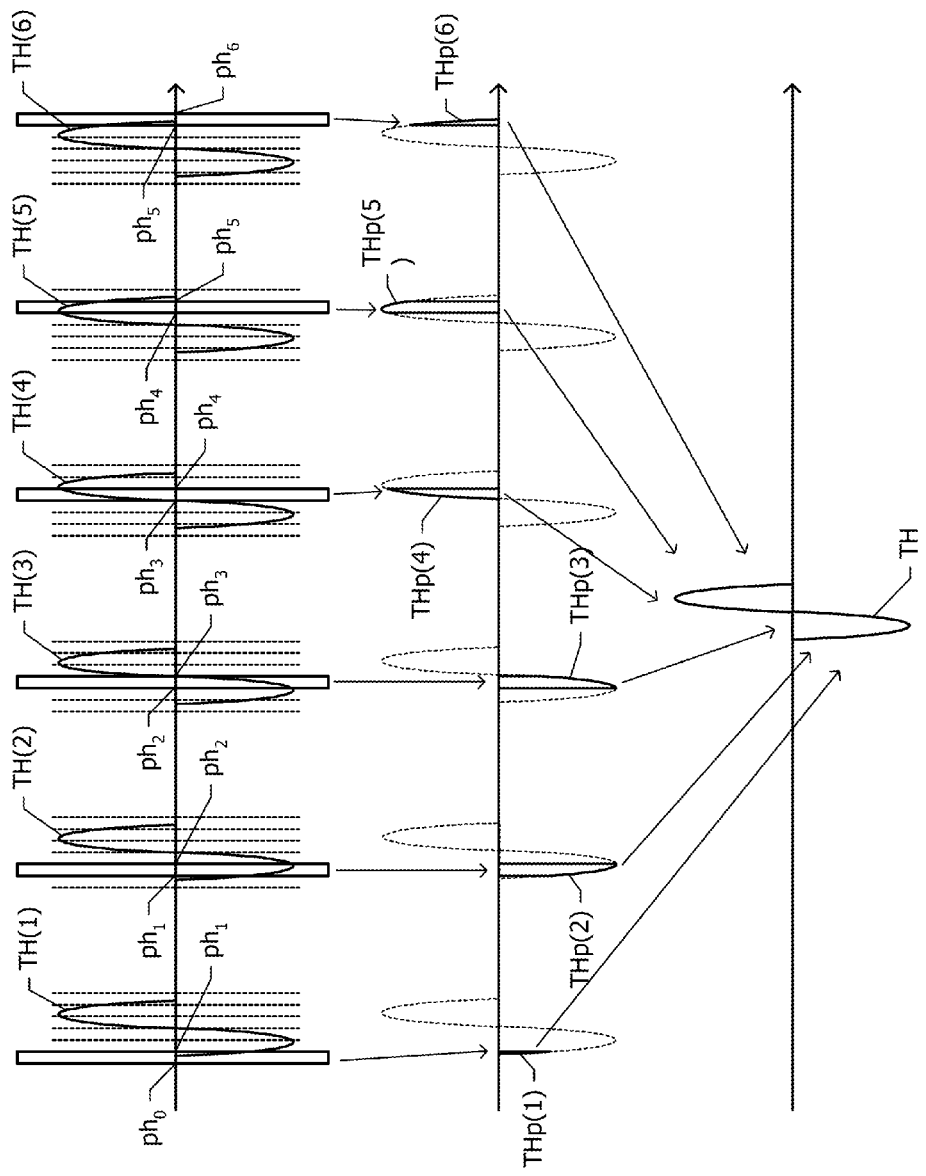
FIG. 15 is a diagram illustrating the waveform of a terahertz wave for explaining a method of measuring a temporal waveform by using the terahertz wave imaging apparatus of the embodiment 6.

FIG. 15 illustrates temporal waveforms TH(1) to TH(6) of the terahertz wave 1 that passed through the measurement target 8. FIG. 15 illustrates waveforms of the terahertz waves 1 corresponding to six laser pulses emitted from the femtosecond laser 20. The temporal waveforms TH(1) to TH(6) of the terahertz waves 1 which respectively correspond to the six laser pulses emitted from the femtosecond laser 20 appear.

When the temporal waveform TH(1) of the terahertz wave 1 is incident upon the electrooptical crystal 3, a delay time of the probe wave 2 relative to the terahertz wave 1 is adjusted so that it is possible to observe the waveform between the phases $ph_0$ and $ph_1$ of the temporal waveform TH(1). Therefore, the partial waveform at the head of the temporal waveform TH(1) between the phases $ph_0$ and $ph_1$ is developed into each cell CL1 to CL5 illustrated in FIG. 2B. For example, a partial waveform THp(1) of the temporal waveform TH(1) between the phases $ph_0$ and $ph_1$ is developed into the cell CL1.

After the partial waveform THp(1) is observed, the movable mirror 32 is moved to prolong the delay time of the probe wave 2 relative to the terahertz wave 1. This delay time is adjusted so that it is possible to observe the waveform between the phases $ph_1$ and $ph_2$ of the temporal waveform TH(1). Therefore, for example, a partial waveform THp(2) of the temporal waveform TH(2) between the phases $ph_1$ and $ph_2$ is developed into the cell CL1.

By repeating motion of the movable mirror 32 and waveform observation of the terahertz wave 1, it is possible to observe partial waveforms of the temporal waveform TH(i)

between phases $ph_{i-1}$ and $ph_i$ by shifting time, where the variable number "i" is a positive integer. FIG. 15 illustrates the temporal waveforms TH(i) and the partial waveforms THp(i) when i=1, 2, . . . , 6.

By coupling obtained partial waveforms THp(1) to THp(6) on a time axis, it is possible to obtain one waveform TH of the terahertz wave 1.

Figure 16:
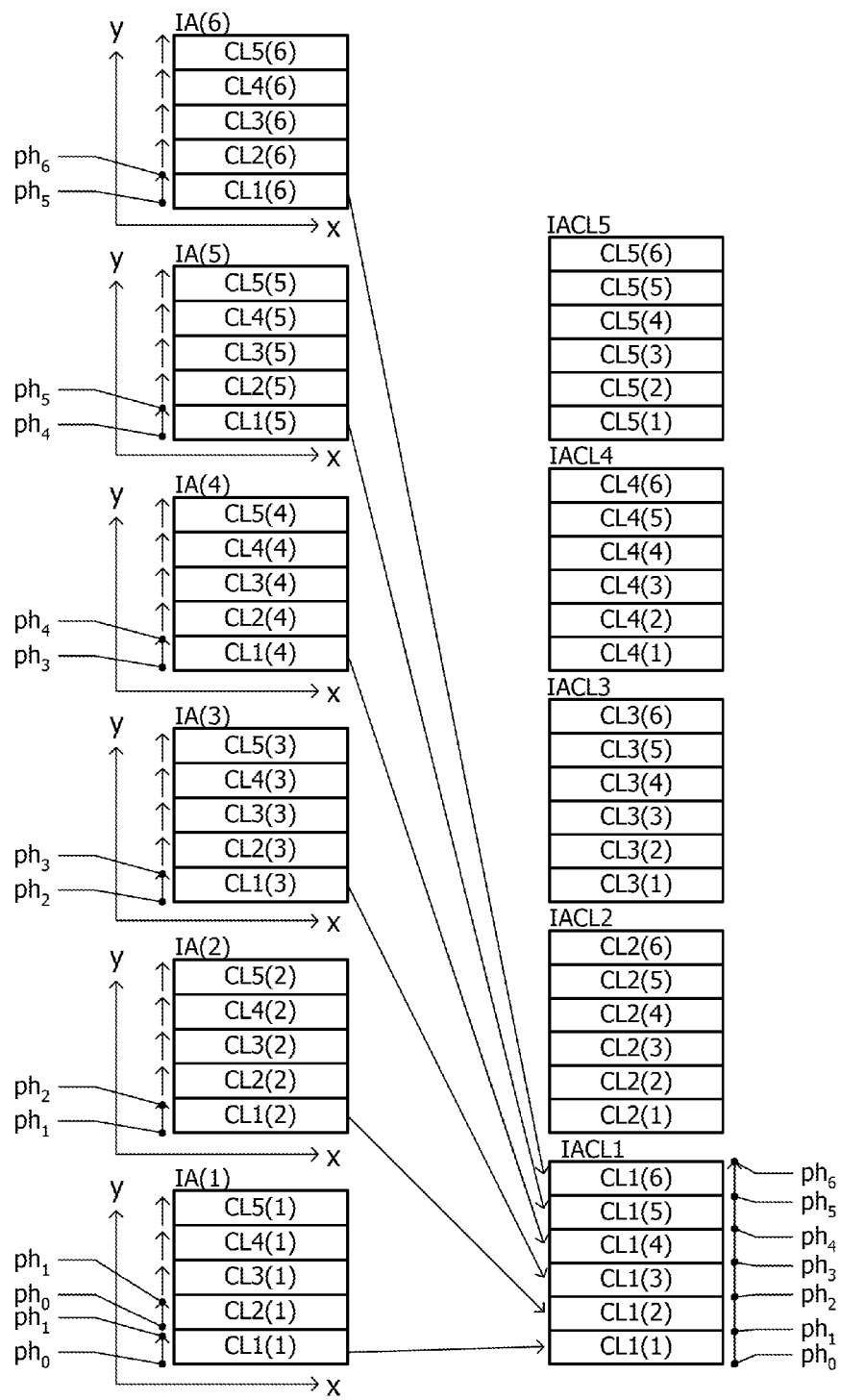
FIG. 16 is a diagram illustrating an imaging plane measured with the terahertz wave imaging apparatus of the embodiment 6.

FIG. 16 is a schematic diagram illustrating image information displayed on the imaging plane of the digital camera 6. The imaging plane is partitioned into five cells CL1 to CL5 as illustrated in FIG. 2B. The waveform information on the temporal waveform TH(1) illustrated in FIG. 15 between the phases $ph_0$ to $ph_1$ is obtained as two-dimensional image information IA(1). With respect to the image information IA(1), the waveform information between the phases $ph_0$ and $ph_1$ is developed into each cell CL1 to CL5 in the y-direction. Similarly, the waveform information between the phases $ph_{i-1}$ and $ph_i$ is obtained as the two-dimensional image information IA(i).

By coupling in the y-axis direction the image information CL1(1) to CL1(6) in the cell CL1 of the two-dimensional image information IA(1) to IA(6), it is possible to obtain two-dimensional image information IACL1 having a time width of the phase between $ph_0$ and $ph_6$. Similarly, it is possible to obtain two-dimensional image information IACL2 to IACL5 of the cells CL2 to CL5 having a time width of the phase between $ph_0$ and $ph_6$.

Even if only a portion of temporal waveform TH of the terahertz wave 1 is able to be measured by one pulse of the probe wave 2, the waveform information of a whole time width of the temporal waveform TH can be obtained using the method of the embodiment 6.

By prolonging the measurable time width of the terahertz wave 1, it is possible to improve a spectrum resolution power. For example, a spectrum resolution power is 0.07 THz when a waveform having a time width of 13.5 psec is measured. If a measurement time width is made longer by seven times, a spectrum resolution power is improved by seven times, namely to 0.01 THz.

In the embodiment 6, the optical system of the example 1 of the embodiment 1 illustrated in FIG. 1 is used as the optical system through which the terahertz wave 1 that passed through the electrooptical crystal 23 passes and the probe wave 2 that passed through the time delay unit 30 passes. Other optical systems may also be adopted including the example 2 of the embodiment 1 illustrated in FIG. 4, the examples 1 to 3 of the embodiment 2 illustrated in FIGS. 5A to 5C, the embodiment 3 illustrated in FIG. 6, the example 1 of the embodiment 4 illustrated in FIG. 7A, the example 2 of the embodiment 4 illustrated in FIG. 9, the embodiment 5 illustrated in FIG. 10, a modification of the embodiment 5 illustrated in FIGS. 11A and 12, and the like.

Figure 17A:
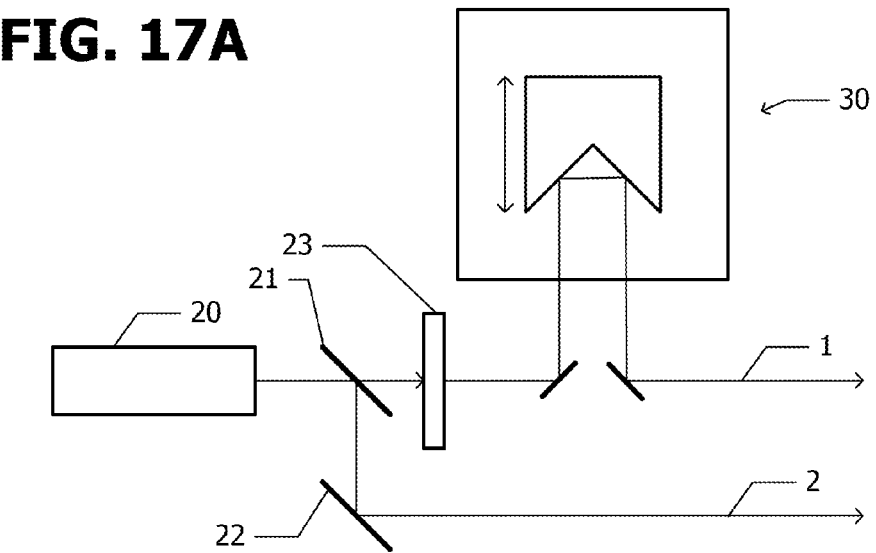
FIGS. 17A and 17B are schematic diagrams illustrating an electromagnetic wave generator unit of the terahertz wave imaging apparatus of first and second modifications of the embodiment 6.

FIG. 17A is a schematic diagram illustrating an electromagnetic wave generator unit of the electromagnetic wave imaging apparatus of the modification 1 of the embodiment 6. Different points from the embodiment 6 illustrated in FIG. 14 will be described mainly. In the modification 1, the time delay unit 30 is disposed on the optical path of the terahertz wave 1.

Figure 17B:
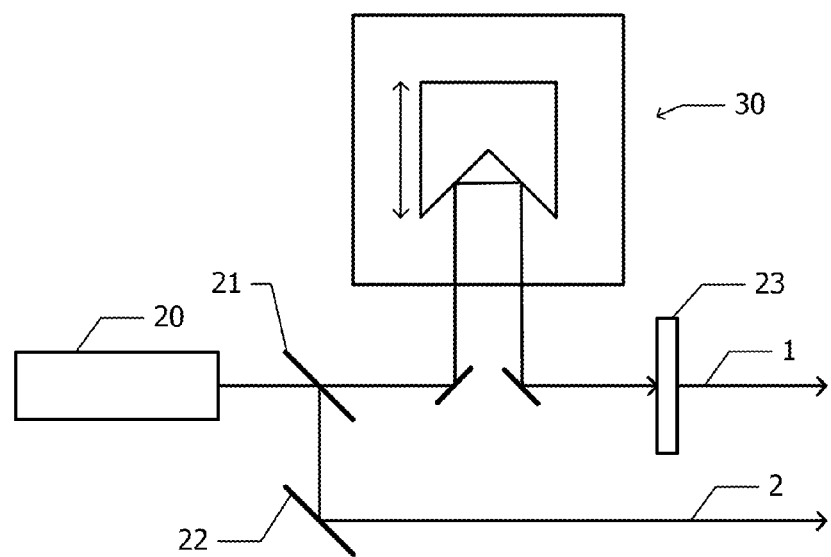

FIG. 17B is a schematic diagram illustrating an electromagnetic wave generator unit of the electromagnetic wave imaging apparatus of the modification 2 of the embodiment 6. Different points from the embodiment 6 illustrated in FIG. 14 will be described mainly. In the modification 2, the time delay unit 30 is disposed on the optical path of the femtosecond laser between the mirror 21 and the electrooptical crystal 23.

In the modifications 1 and 2, it is possible to adjust a delay time of the terahertz wave 1 relative to the probe wave 2. In other words, it is possible to adjust a relative phase relation between the terahertz wave 1 and the probe wave 2. As in the case of the embodiment 6, it is therefore possible to make long the time width capable of measuring the waveform of terahertz wave 1.

Embodiment 7

Figure 18A:
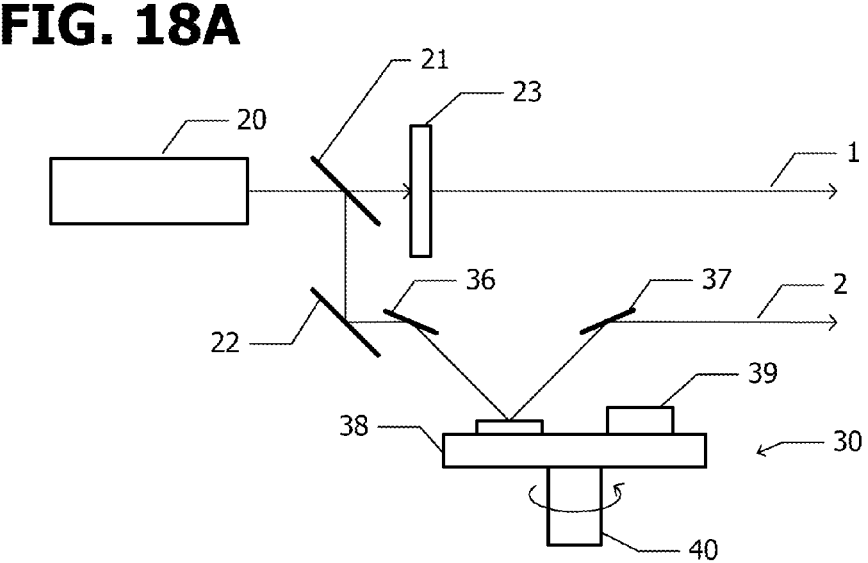
FIG. 18A is a schematic diagram illustrating an electromagnetic wave generator unit of the terahertz wave imaging apparatus an embodiment 7.

FIG. 18A is a schematic diagram illustrating an electromagnetic wave generator unit of the electromagnetic wave imaging apparatus of the embodiment 7. Different points from FIG. 14 of the embodiment 6 will be described.

As in the case of the embodiment 6, in the embodiment 7, the time delay unit 30 is disposed on the optical path of the probe wave 2. In the embodiment 7, the time delay unit 30 includes mirrors 36 and 37, a rotary stage 38, a plurality of movable mirrors 39 and a motor 40.

Figure 18B:
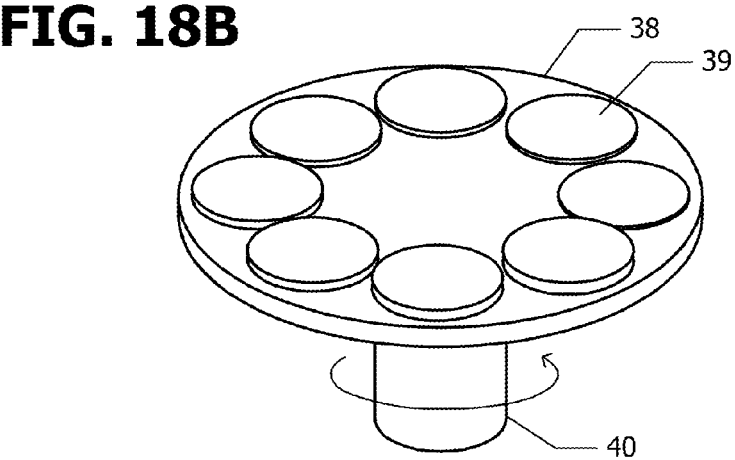
FIG. 18B is a perspective view illustrating the main portion of a time delay unit.

FIG. 18B is a perspective view illustrating the main portion of the time delay unit 30. A motor 40 rotates the rotary stage 38. A plurality of movable mirrors 39 is disposed on the rotary stage 38 along a circumference of a circle, the center of which coincides with the rotation center of the rotary stage 38. A reflection plane of each movable mirror 39 is perpendicular to the rotation axis of the rotary stage 38. Heights of the reflection planes of the movable mirrors 39 are different from each other.

As illustrated in FIG. 18A, the probe wave 2 reflected at the mirror 22 is reflected at the mirror 36. The probe wave 2 reflected at the mirror 36 is reflected by the movable mirror 39 and propagates toward the mirror 37. The optical path of the probe wave 2 reflected at the mirror 37 is the same as the embodiment 6 illustrated in FIG. 14.

It is possible to change the optical path length of the probe wave 2 by rotating the rotary stage 38 and stopping it in such a manner that one of the movable mirrors 39 is disposed on the optical path of the probe wave 2. A delay time of the probe wave 2 relative to the terahertz wave 1 is able to be changed.

As in the case of the embodiment 6, also in the embodiment 7, it is possible to make long the time width for measuring the waveform of the terahertz wave 1. As compared to the embodiment 6 using the linear motion stage 34, by using the rotary stage 38, the time for adjusting the delay time can be made short.

The time delay unit 30 used in the embodiment 7 may be disposed on the optical path of the terahertz wave 1 as illustrated in FIG. 17A, or may be disposed on the optical path of the femtosecond laser between the mirror 21 and the electrooptical crystal 23 as illustrated in FIG. 17B.

As in the case of the embodiment 6, as the optical system through which the terahertz wave 1 that passed through the electrooptical crystal 23 passes and the probe wave 2 that passed through the time delay unit 30 passes, the optical systems other than that of the example 1 of the embodiment 1 illustrated in FIG. 1 may also be used. For example, the optical system of the example 2 of the embodiment 1 illustrated in FIG. 4, the examples 1 to 3 of the embodiment 2 illustrated in FIGS. 5A to 5C, the embodiment 3 illustrated in FIG. 6, the example 1 of the embodiment 4 illustrated in FIG. 7A, the example 2 of the embodiment 4 illustrated in FIG. 9, the embodiment 5 illustrated in FIG. 10, and the modifications of the embodiment 5 illustrated in FIGS. 11A and 12, or the like may be used.

Embodiment 8

Figure 19A:
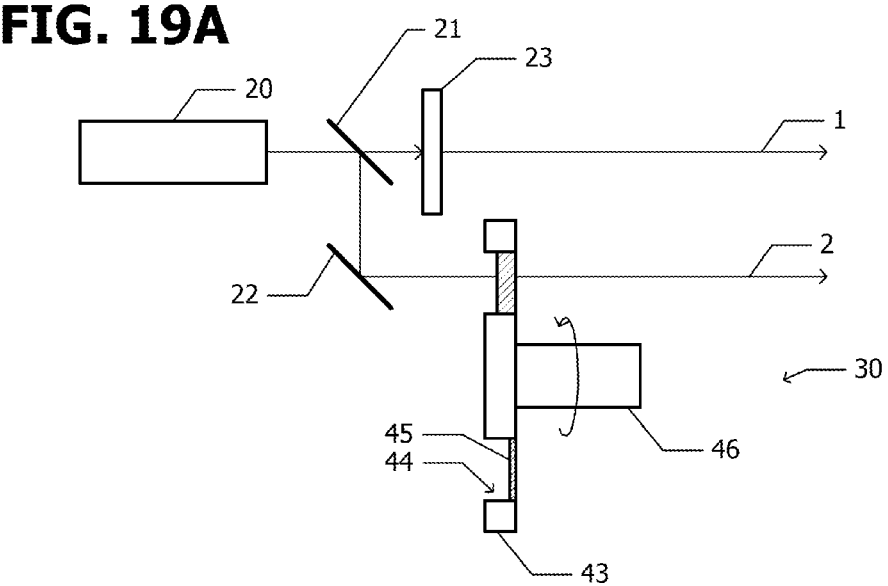
FIG. 19A is a schematic diagram illustrating an electromagnetic wave generator unit of the terahertz wave imaging apparatus of an embodiment 8.

FIG. 19A is a schematic diagram illustrating an electromagnetic wave generator unit of the electromagnetic wave imaging apparatus of the embodiment 8. Different point from the embodiment 6 illustrated in FIG. 14 will be described mainly.

In the embodiment 8, as in the case of the embodiment 6, the time delay unit 30 is disposed on the optical path of the probe wave 2. In the embodiment 8, the time delay unit 30 includes a rotary plate 43 having a plurality of openings 44, a transparent plate 45 and a motor 46. The motor 46 rotates the rotary plate 43 and stops the rotary plate 43 at a desired position.

Figure 19B:
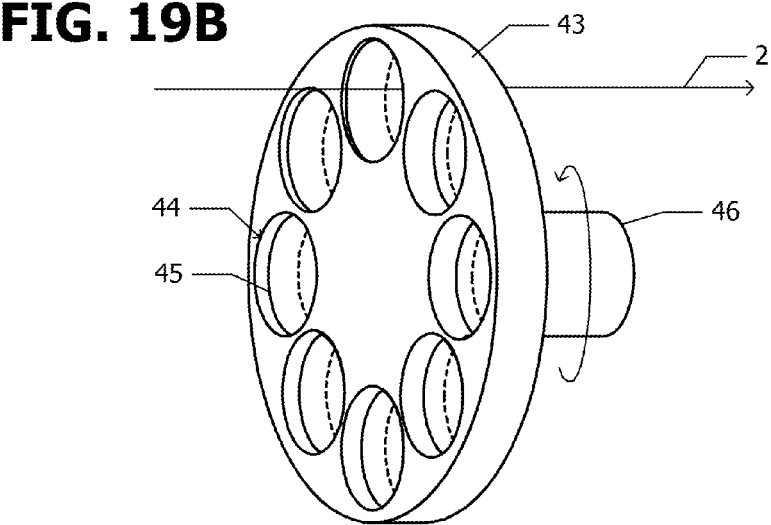
FIG. 19B is a perspective view illustrating the main portion of a time delay unit.

As illustrated in FIG. 19B, the openings 44 are disposed on a circumference of a circle, the center of which coincides with the rotation center of the rotary plate 43. Each opening 44 is covered with the transparent plate 45. Thicknesses of a plurality of transparent plates 45 are different from each other. Glass plates (e.g., BK7) are used for the transparent plates 45.

A desired one of the transparent plates 45 can be disposed on the optical path of the probe wave 2 by rotating the motor 46. As the thickness of the transparent plate 45 disposed on the optical path of the probe wave 2 changes, the optical path length of the probe wave 2 changes so that the delay time of the probe wave 2 relative to the terahertz wave 1 is able to be adjusted.

The structure of the optical system through which the terahertz wave 1 that passed through the electrooptical crystal 23 passes and the probe wave 2 that passed through the transparent plate 45 passes is the same as the optical system of the example 1 of the embodiment 2 illustrated in FIG. 5A.

As in the case of the embodiment 6, also in the embodiment 8, it is possible to make long a time width for measuring the waveform of the terahertz wave 1. As compared to the embodiment 6 using the liner motion stage 34, the time for adjusting the delay time can be made short by using the rotary plate 43.

Under the condition that the delay time of the probe wave 2 relative to the terahertz wave 1 is fixed, the case will be considered in which the optical system is structured so that it is possible to obtain the temporal waveform having a time width of 1.6 psec at fourteen positions arranging in the width direction of the measurement target 8 at the same time. For example, a transparent plate 45 having a thickness of 2 mm is disposed on the optical path of the probe wave 2 to obtain the temporal waveform having a time width of 1.6 psec. Thereafter, the rotary plate 43 is rotated to dispose another transparent plate 45 having a thickness of 2.941 mm, and the temporal waveform having a time width of 1.6 psec continuing the temporal waveform that has measured at a previous time can be measured.

By changing eight transparent plates 45 having a thickness difference of 0.941 mm to sequentially obtain temporal waveforms of the terahertz wave 1, the temporal waveform having a time width of 12.8 psec can be obtained.

The time delay unit 30 of the embodiment 8 may be disposed on the optical path of the femtosecond laser between the mirror 21 and the electrooptical crystal 23 as illustrated in FIG. 17B.

As the optical system through which the terahertz wave 1 that passed through the electrooptical crystal 23 passes and the probe wave 2 that passed through the time delay unit 30 passes, the optical systems other than that of the example 1 of the embodiment 2 illustrated in FIG. 5A may also be used. For example, the optical system of the example 1 of the embodiment 1 illustrated in FIG. 14, the example 2 of the embodiment 1 illustrated in FIG. 4, the examples 2 to 3 of the embodiment 2 illustrated in FIGS. 5B to 5C, the embodiment 3 illustrated in FIG. 6, the example 1 of the embodiment 4 illustrated in FIG. 7A, the example 2 of the embodiment 4 illustrated in FIG. 9, the embodiment 5 illustrated in FIG. 10, and the modifications of the embodiment 5 illustrated in FIGS. 11A and 12, or the like may be used.

Embodiment 9

Figure 20A:
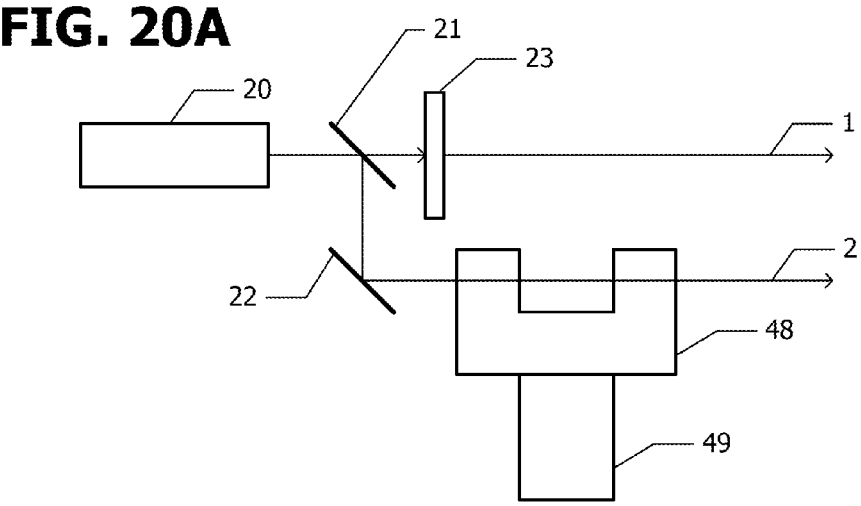
FIG. 20A is a schematic diagram illustrating an electromagnetic wave generator unit of the terahertz wave imaging apparatus of an embodiment 9.

FIG. 20A is a schematic diagram illustrating an electromagnetic wave generator unit of the electromagnetic wave imaging apparatus of the embodiment 9. Different points from the embodiment 9 in FIGS. 19A and 19B will be described mainly.

As illustrated in FIG. 20A, the time delay unit 30 of the embodiment 9 includes a rotary transparent block 48 and a motor 49. The rotary transparent block 48 includes a disc shaped base plate, and a cylindrical side wall disposed along the outer circumference of the base plate.

Figure 20B:
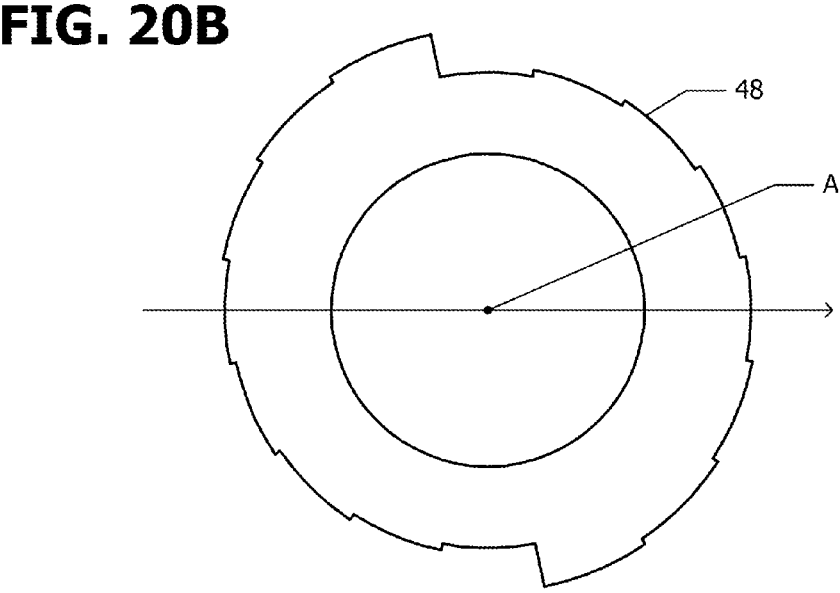
FIG. 20B is a plan view illustrating the main portion of a time delay unit.

As illustrated in FIG. 20B, the inner circumferential surface of the side wall has a cylindrical shape having a constant diameter. The outer circumferential surface of the side wall has a cylindrical shape having a stepwise changing diameter with respect to a circumferential direction. A thickness of the side wall changes stepwise with respect to the circumferential direction. The motor 49 rotates the rotary transparent block 48 by using the center axis of the inner circumferential surface of the side wall of the rotary transparent block 48 as the rotation center, and stops the rotary transparent block 48 at a desired position.

An optical path of the probe wave 2 crosses at a right angle the center axis A of the inner circumferential surface of the side wall of the rotary transparent block 48. Namely, the probe wave 2 passes the side wall of the rotary transparent block 48 in the radial direction. Since the thickness of the side wall changes stepwise, as the rotary transparent block 48 rotates, it becomes possible to change a thickness of the side wall through which the probe wave 2 passes. The optical path length of the probe wave 2 changes and it becomes possible to change the delay time relative to the terahertz wave 1.

Since the inner circumferential surface of the side wall of the rotary transparent block 48 is cylindrical, and the outer circumferential surface is partially cylindrical, even if there is some error of position alignment of the rotary transparent block 48 in the rotation direction, the propagation direction and the optical path length of the probe wave 2 are not influenced.

A plan cross section of the inner circumferential surface of the side wall may be polygonal, and the outer circumferential surface may be constituted of a plurality of plain surfaces having different heights from the corresponding plain surfaces constituting the inner circumferential surface. In this case, the side wall of the rotary transparent block 48 does not condense and disperse the probe wave 2. Since the probe wave 2 have to be vertically incident upon each plain surface, it is desired to improve a position precision of the rotary transparent block 48 in the rotation direction.

Embodiment 10

Figure 21:
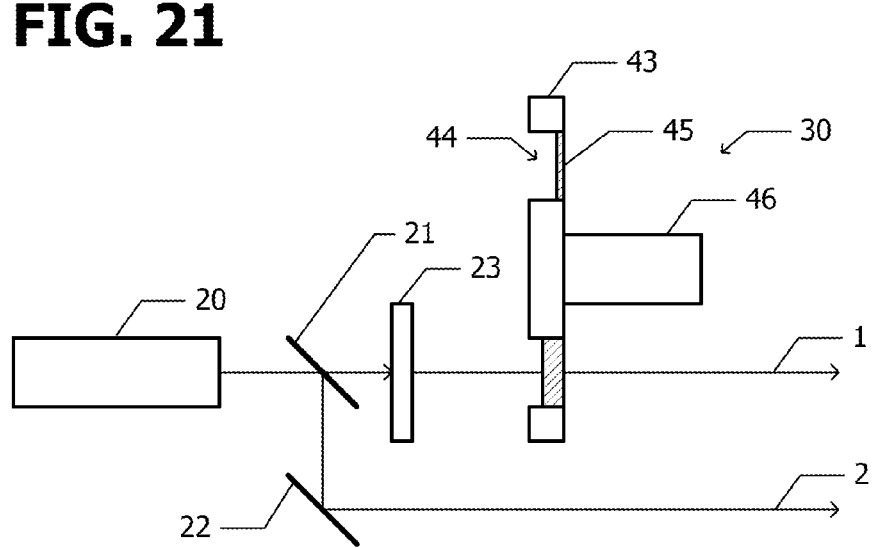
FIG. 21 is a schematic view illustrating an electromagnetic wave generator unit of the terahertz wave imaging apparatus of an embodiment 10.

FIG. 21 is a schematic diagram of an electromagnetic wave generator unit of the electromagnetic wave imaging apparatus of the embodiment 10. Different points from the embodiment 8 in FIGS. 19A and 19B will be described mainly.

In the embodiment 8, the time delay unit 30 is disposed on the optical path of the probe wave 2. In the embodiment 10, the time delay unit 30 is disposed on the optical path of the terahertz wave 1. The structure of the time delay unit 30 is the same as that of the embodiment 8. The transparent plates 45 are made of material transparent in the wave length range of the terahertz wave 1 such as polyethylene. A refractive index of polyethylene in the wavelength range of the terahertz wave 1 is 1.37. Eight polyethylene transparent plates 45 having different thicknesses at a step size of 1.297 mm covers the openings 44 of the rotary plate 43. The same temporal waveforms as that of the embodiment 8 can be obtained.

Embodiment 11

Figure 22:
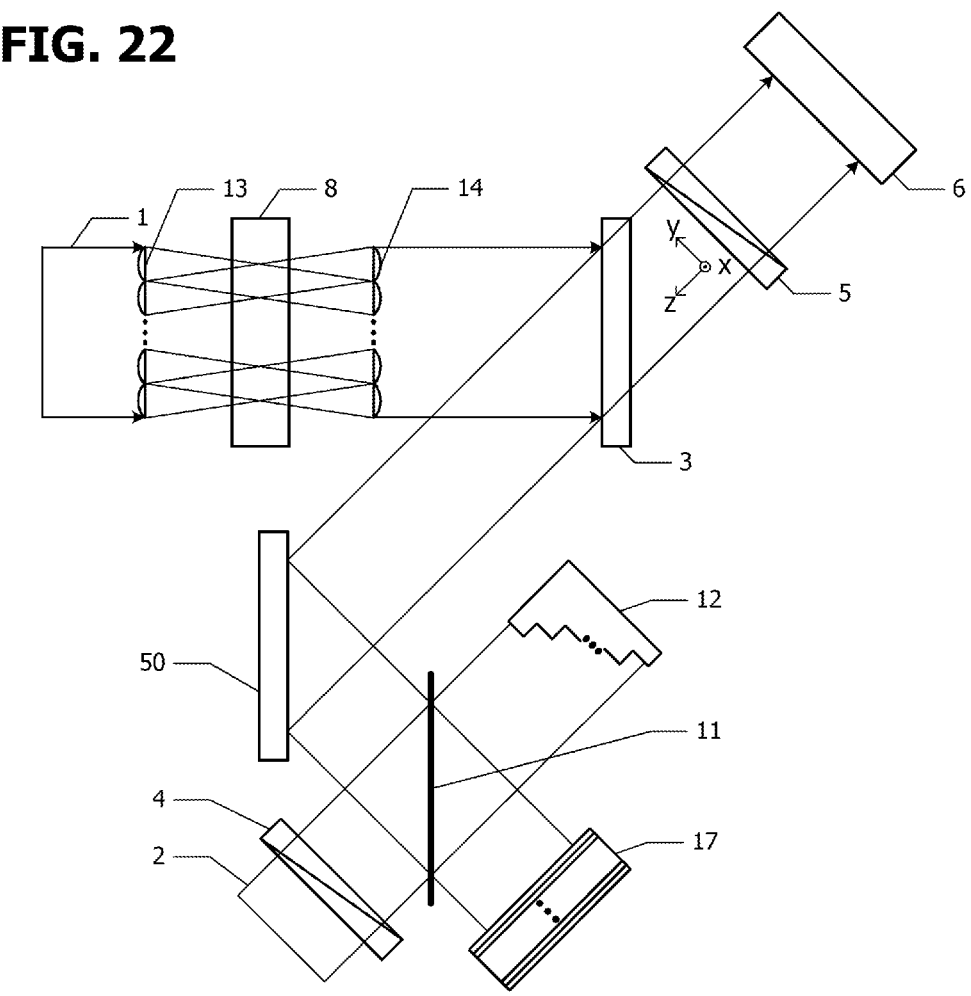
FIG. 22 is a schematic diagram illustrating a terahertz wave imaging apparatus of an embodiment 11.

FIG. 22 is a schematic diagram illustrating an electromagnetic wave imaging apparatus of the embodiment 11. Different points from the embodiment 5 in FIG. 10 will be described mainly.

In the embodiment 11, a deformable mirror device (DMD) 50 is disposed on the optical path of the probe wave 2 between the beam splitter 11 and the electrooptical crystal 3. The probe wave 2 that passed through the beam splitter 11 is reflected at DMD 50 and incident upon the electrooptical crystal 3.

As in the case of the embodiment 5, in the embodiment 11, the imaging plane of the digital camera 6 is partitioned into a plurality of cells CL (FIG. 8A) disposed in a matrix shape. DMD 50 has a plurality of movable mirrors disposed in a matrix shape. By moving each movable mirror in a direction perpendicular to the reflection plane, it is possible to change an optical path length of the probe wave 2 for each area corresponding to the movable mirror. The movable mirror is prepared at least each cell defined in the imaging plane. For example, if cells are disposed in a matrix having 14 rows and 14 columns, movable mirrors are disposed at least in a matrix having 14 rows and 14 columns. A plurality of movable mirrors may be disposed for each cell. For example, movable mirrors may be disposed in a matrix having 28 rows and 28 columns or 42 rows and 42 columns.

The actual shape of the y-direction step-like mirror 12 and the x-direction step-like mirror array 17 is not perfectly coincident with the design shape because of manufacturing variations or the like. This shape variation shifts the optical path length of the probe wave 2 from a desired length. It is possible to compensate the shift of the optical path length by adjusting the position of the movable mirror of the DMD 50. The DMD 50 for compensating the shift of the optical path length in a beam cross section may be called a "spatial optical modulator".

Since it is possible to bring the delay time of the probe wave 2 close to a design value, it is possible to reduce a measurement error of the temporal waveform of the terahertz wave 1. The DMD 50 may be disposed on the optical path of the probe wave 2 in the example 1 of the embodiment 1 illustrated in FIG. 1. In the example 2 of the embodiment 1 illustrated in FIG. 4, the DMD 50 may be disposed on the optical path of the terahertz wave 1.

Embodiment 12

Figure 23:
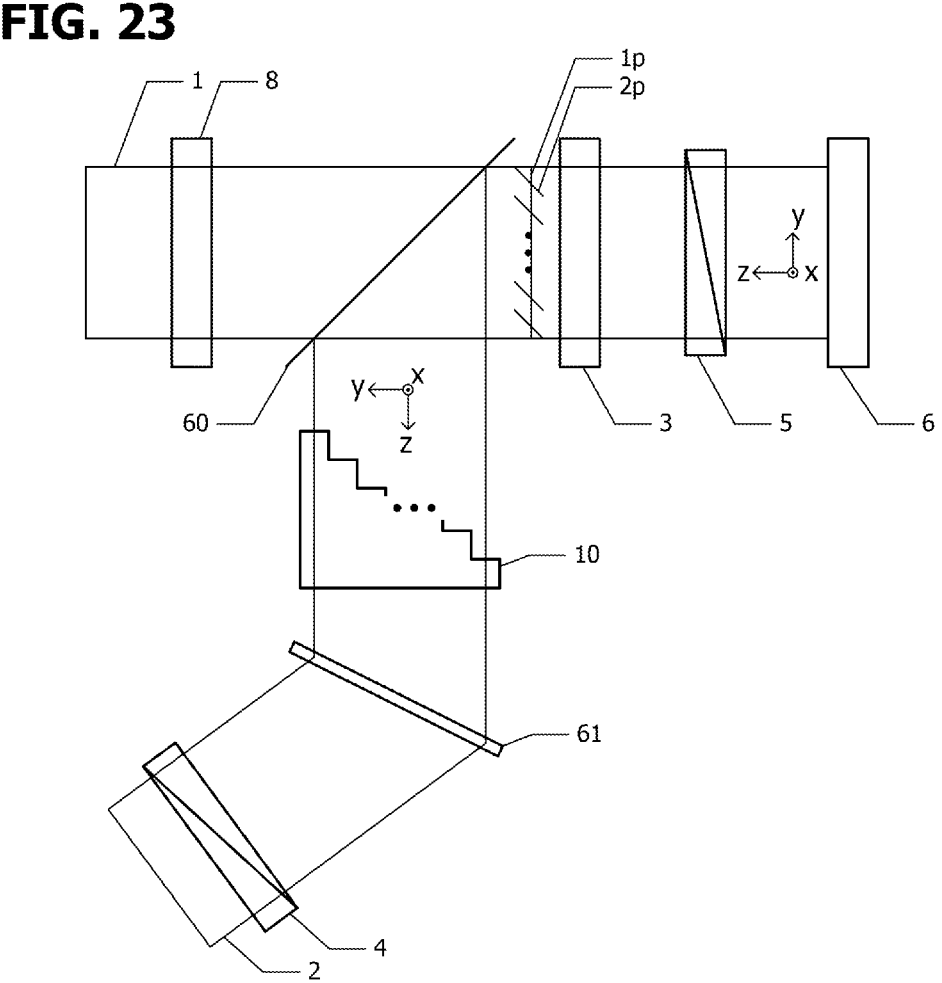
FIG. 23 is a schematic diagram illustrating a terahertz wave imaging apparatus of an embodiment 12.

FIG. 23 is a schematic diagram illustrating an electromagnetic wave imaging apparatus of the embodiment 12. In the embodiments 1 to 11, the terahertz wave 1 and the probe wave 2 are noncoaxially incident upon the electrooptical crystal 3. In the embodiment 12, both are coaxially incident upon the electrooptical crystal 3. The structure of the electromagnetic wave generator unit for generating the terahertz wave 1 and the probe wave 2 is the same as that of the embodiment 1 illustrated in FIG. 1 or the same as that of the embodiment 6 illustrated in FIG. 14. The electromagnetic wave generator unit may have the structure illustrated in FIG. 17A, FIG. 17B, FIG. 18A, FIG. 19A, FIG. 20A or FIG. 21.

The terahertz wave 1 passes through the measurement target 8, and then through a pellicle beam splitter 60 and is vertically incident upon the electrooptical crystal 3. The terahertz wave 1 has uniform phases in the beam cross section, and the pulse plane $1p$ is perpendicular to the propagation direction. The "pulse plane" means a plane linking the peak positions of intensity of the pulse beam. As an optical beam passes through a diffraction grating, the pulse plane is not parallel to the wave front (equiphase plane). The wave front is always perpendicular to the optical beam propagation direction.

The probe wave 2 that passed through the polarizer 4 is diffracted by a transmission type diffraction grating 61. The diffracted probe wave 2 passes through the step-like transparent block 10, and is reflected at the pellicle beam splitter 60 and then is vertically incident upon the electrooptical crystal 3. A reflection plane of the pellicle beam splitter 60 is parallel to the x-axis direction. The terahertz wave 1 that passed through the pellicle beam splitter 60 and the probe wave 2 reflected by the pellicle beam splitter 60 become a coaxial optical flux to be vertically incident upon the electrooptical crystal 3.

The probe wave 2 that passed through the electrooptical crystal 3 passes through the analyzer 5, and is incident upon the digital camera 6. Also in the area where the probe wave 2 before being reflected at the pellicle beam splitter 60 propagates, an xyz coordinate system is defined in which a direction opposite to the propagation direction is defined as a positive direction of the z-axis. The x-axes of the xyz coordinate system before and after being reflected at the pellicle beam splitter 60 are parallel to each other.

Figure 24:
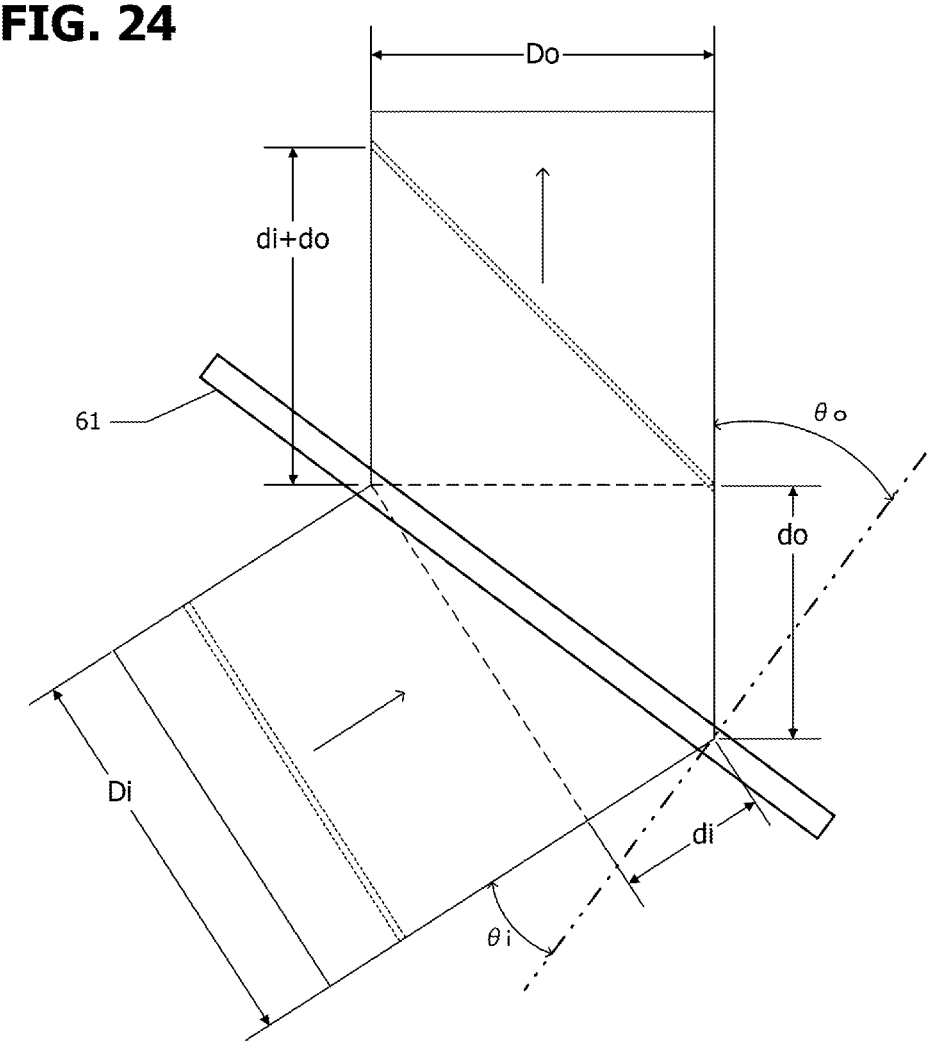
FIG. 24 is a schematic diagram illustrating a relation between a transmission type diffraction grating of the terahertz wave imaging apparatus of the embodiment 12 and a beam path.

The relation between the incident beam and the diffracted beam passing the transmission type diffraction grating 61 will be described by referring to FIG. 24. The number of grooves per unit length of the transmission type diffraction grating 61 is represented by N, a diffraction order is represented by k, and an incident beam wave length is represented by λ. The following relation stands between an incident angle θi and a diffraction angle θo.

$$\sin(\theta i) + \sin(\theta o) = Nk\lambda$$

If the number N of grooves of the transmission type diffraction grating 61 is 1000/mm, an incident angle θi is 10°, and a first order diffraction beam (k=1) is used, then a diffraction angle θo is 38.78°. The following relation stands between an incident beam width Di and an outgoing beam width Do.

$$Di/\cos(\theta i) = Do/\cos(\theta o)$$

If an incident beam width Di is 38 mm, an outgoing beam width Do is 30 mm. The pulse plane of the incident beam is perpendicular to the propagation direction of the incident beam. The pulse plane of the diffracted beam is inclined relative to the propagation direction. A time difference when opposite ends of the pulse plane of the diffracted beam reach the virtual plane perpendicular to the propagation direction is:

$$(di+do)/c$$

where c is a light speed, $$di = Di \times \tan(\theta i)$$

$$do = Do \times \tan(\theta o).$$

In the above example, a time difference (di+do)/c is 102.89 psec. The pulse plane of the probe wave 2 is incident upon the step-like transparent block 10 illustrated in FIG. 23 in the state where the pulse plane is slanted relative to the propagation direction. Each pulse plane of the probe wave 2 that passed through the tread face (unit area) is also slanted relative to the propagation direction.

As illustrated in FIG. 23, the pulse plane 1p of the terahertz wave 1 is vertical to the propagation direction (z-direction), and the pulse plane 2p of the probe wave 2 corresponding to each tread face (unit area) is slanted relative to the propagation direction in front of the electrooptical crystal 3. The step (height of the riser face) of the step-like transparent block 10 is designed so that the front ends of the pulse planes of all unit areas reach the electrooptical crystal 3 at the same time. The operation and effect like those of the embodiment 1 illustrated in FIG. 2A are obtained.

In the case where a refractive index of the step-like transparent block 10 is 1.51, a width (size in the y-direction) of each step (tread face) is 6.00 mm, and a step (height of the riser face) is 12.05 mm, it is possible to measure a temporal waveform of the terahertz wave 1 having a resolution power of 0.20 psec and a time width of 20.58 psec at five positions in the width direction (y-direction) of the measurement target 8. This corresponds to a spectroscopic performance of a resolution power of 0.049 THz and a bandwidth of 2.5 THz.

In the embodiment 12, the transmission type diffraction grating 61 is used in order to slant the pulse plane of the probe wave 2 relative to the propagation direction. Instead of the transmission type diffraction grating 61, a prism may be used. In the case where a prism is used, a refractive index and wavelength dispersion of optical material, a prism angle, an incident angle and the like are designed to obtain a desired slant for the pulse plane.

Although the pellicle beam splitter is used for making the terahertz wave 1 and the probe wave 2 to be coaxial beams, another optical device for transmitting the terahertz wave 1 and reflecting the probe wave 2. For example, a silicon substrate may be used. By reflecting the terahertz wave 1 and transmitting the probe wave 2, both of them may be made coaxial. For example, an optical device having a glass plate coated with a transparent material such as indium tin oxide (ITO) and indium zinc oxide (IZO).

Although the terahertz wave is used as an electromagnetic wave for detecting the measurement target in the above embodiments, the electromagnetic wave is not limited to the terahertz wave if the electromagnetic wave can detect the measurement target. It is sufficient that if the transparent material is transparent in the target wavelength region. It is not necessary that the transparent material is transparent in a visible range.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment(s) of the present invention have been described in detail, it should be understood that the various changes, substitutions, and alterations could be made hereto without departing from the spirit and scope of the invention.

What is claimed is:

1. An electromagnetic wave imaging apparatus comprising:
    an electrooptical crystal;
    a first optical system irradiating a measurement target with a pulsed detecting electromagnetic wave and making the detecting electromagnetic wave that is transmitted through or reflected by the measurement target incident upon the electrooptical crystal;
    a second optical system slanting a pulse plane of a pulsed probe wave for imaging relative to a pulse plane of the detecting electromagnetic wave and making the probe wave incident upon the electrooptical crystal;
    a camera detecting the probe wave passing through the electrooptical crystal; and
    a phase shifting component generating a plurality of optical path length differences in a direction perpendicular to a virtual plane, included in the first or second optical system,
    wherein the first optical system or the second optical system includes a compensating optical component which partitions a beam cross section of the detecting electromagnetic wave or the probe wave into a plurality of unit areas in the virtual plane perpendicular to a pulse plane of the detecting electromagnetic wave and to a pulse plane of the probe wave, the optical component making different an optical path length of a beam passing each unit area and compensating a phase shifting between the pulse plane of the detecting electromagnetic wave and the pulse plane of the probe wave at a plurality of positions in a crossing direction of a surface of the electrooptical crystal and the virtual plane, and
    wherein the compensating optical component includes two step-like mirrors having a plurality of reflection planes, sizes and positions of which are different from each other in a beam propagation direction with respect to a width direction and a length direction of the electromagnetic wave or the probe wave.

2. The electromagnetic wave imaging apparatus according to claim 1, wherein the first optical system and the second optical system slant the pulse plane of the probe wave for imaging relative to the pulse plane of the detecting electromagnetic wave by making the detecting electromagnetic wave and the probe wave noncoaxially incident upon the electrooptical crystal.

3. The electromagnetic wave imaging apparatus according to claim 1, wherein the second optical system includes a pulse plane slanting optical element that slants the pulse plane of the probe wave relative to a plane perpendicular to a propagation direction, and the first optical system and the second optical system make the detecting electromagnetic wave and the probe wave coaxially incident upon the electrooptical crystal.

4. The electromagnetic wave imaging apparatus according to claim 1, further comprising a cylindrical lens train disposed in said first optical system for condensing said detecting electromagnetic wave into a plurality of lineal regions, and applying the detecting electromagnetic wave to said measurement target.

5. The electromagnetic wave imaging apparatus according to claim 1, wherein the first optical system or the second optical system further includes a time delay unit varying a delay time of one of the pulse plane of the electromagnetic wave and the pulse plane of the probe wave relative to the other of the pulse plane of the electromagnetic wave and the pulse plane of the probe wave.

6. The electromagnetic wave imaging apparatus according to claim 1, wherein the first optical system or the second optical system further includes a spatial optical modulator varying an optical path length of each of a plurality of areas defined in a beam cross section of the detecting electromagnetic wave or the probe wave.

7. The electromagnetic wave imaging apparatus according to claim 1, further comprising:
    a femtosecond laser;

a beam splitter branching a beam that is output from the femtosecond laser into the probe wave and a first wave; and a terahertz wave generator unit generating a terahertz wave as the detecting electromagnetic wave by irradiating another electrooptical crystal with the first wave.

8. The electromagnetic wave imaging apparatus according to claim 1, wherein the partitioned beams are obliquely incident upon the electrooptical crystal, and the partitioned beams are in phase at a surface of the electrooptical crystal.

* * * * *